US010631749B2

(12) United States Patent
Rubenstein

(10) Patent No.: US 10,631,749 B2
(45) Date of Patent: Apr. 28, 2020

(54) DEVICES AND METHODS FOR MAPPING CARDIAC ARRHYTHMIA

(71) Applicant: Greenville Health System, Greenville, SC (US)

(72) Inventor: Donald S. Rubenstein, Greenville, SC (US)

(73) Assignee: Health Sciences Center, LLC, Greenville, SC (US)

( * ) Notice: Subject to any disclaimer, the term of this patent is extended or adjusted under 35 U.S.C. 154(b) by 84 days.

(21) Appl. No.: 15/750,358

(22) PCT Filed: Aug. 4, 2016

(86) PCT No.: PCT/US2016/045483
§ 371 (c)(1),
(2) Date: Feb. 5, 2018

(87) PCT Pub. No.: WO2017/024107
PCT Pub. Date: Feb. 9, 2017

(65) Prior Publication Data
US 2018/0235495 A1 Aug. 23, 2018

Related U.S. Application Data

(60) Provisional application No. 62/201,874, filed on Aug. 6, 2015.

(51) Int. Cl.
*A61B 5/04* (2006.01)
*A61B 5/042* (2006.01)
(Continued)

(52) U.S. Cl.
CPC .............. *A61B 5/0422* (2013.01); *A61B 5/00* (2013.01); *A61B 5/042* (2013.01); *A61B 5/046* (2013.01);
(Continued)

(58) Field of Classification Search
CPC ..... A61B 5/0422; A61B 5/6859; A61B 5/046; A61B 5/6858; A61B 5/6857; A61B 5/00;
(Continued)

(56) References Cited

U.S. PATENT DOCUMENTS 4,962,767 A * 10/1990 Brownlee .............. A61N 1/056
600/509
5,041,973 A * 8/1991 Lebron .............. A61B 5/04021
703/11
(Continued)

FOREIGN PATENT DOCUMENTS

WO   WO 95/10979   4/1995

OTHER PUBLICATIONS

Allessie et al. Experimental evaluation of Moe's multiple wavelet hypothesis of atrial fibrillation. In: Zipes DP, Jalife J, (ed), Cardiac electrophysiology and arrhythmias, Orlando, Grune and Stratton, 1985, pp. 265-275.
(Continued)

*Primary Examiner* — Mallika D Fairchild
(74) *Attorney, Agent, or Firm* — Dority & Manning, P.A.

(57) ABSTRACT

Cardiac mapping catheters and methods for using the catheters are described. The catheter can detect the presence, direction and/or source of a depolarization wave front associated with cardiac arrhythmia. A mapping catheter includes a plurality of bipolar electrode pairs in which the members of each pair are opposed to one another across a perimeter, for instance in a circular pattern. The spaced arrangement of the electrodes can be utilized to identify directional paths of moving electric fields or wave fronts in any direction passing across the endocardial surface. The catheters can be used to identify locations and types of triggers and/or drivers of cardiac arrhythmia including rotors, ectopic trigger foci and/or to delineate reentrant pathways.

16 Claims, 14 Drawing Sheets

(51) Int. Cl.

| | |
|---|---|
| *A61B 18/14* | (2006.01) |
| *A61B 5/00* | (2006.01) |
| *A61B 5/0452* | (2006.01) |
| *A61B 5/0408* | (2006.01) |
| *A61B 5/046* | (2006.01) |
| *A61B 18/00* | (2006.01) |
| *A61B 18/18* | (2006.01) |

(52) U.S. Cl.
CPC .......... *A61B 5/0408* (2013.01); *A61B 5/0452* (2013.01); *A61B 5/6857* (2013.01); *A61B 5/6858* (2013.01); *A61B 5/6859* (2013.01); *A61B 18/1492* (2013.01); *A61B 2018/00267* (2013.01); *A61B 2018/00821* (2013.01); *A61B 2018/00839* (2013.01); *A61B 2018/1807* (2013.01); *A61B 2218/002* (2013.01)

(58) Field of Classification Search
CPC ..... A61B 5/0452; A61B 5/042; A61B 5/0408; A61B 2018/1807; A61B 2018/00839; A61B 2018/00821; A61B 2018/00267; A61B 2218/002
See application file for complete search history.

(56) References Cited

U.S. PATENT DOCUMENTS

| | | | |
|---|---|---|---|
| 5,755,664 A | 5/1998 | Rubenstein | |
| 5,848,972 A * | 12/1998 | Triedman | A61B 5/0422 600/508 |
| 6,702,811 B2 * | 3/2004 | Stewart | A61B 18/1492 606/41 |
| 6,799,064 B1 | 9/2004 | Hassett | |
| 2013/0345537 A1 | 12/2013 | Thakur et al. | |
| 2014/0200575 A1 * | 7/2014 | Spector | A61B 5/04014 606/40 |
| 2016/0317094 A1 * | 11/2016 | Byrd | A61B 5/6858 |

OTHER PUBLICATIONS

Allessie et al. Circus movement in rabbit atrial muscle as a mechanism of tachycardia: III—the "leading circle" concept: A new model of circus movement in cardiac tissue without the involvement of an anatomical obstacle. *Circ Res.* 1977; 41:9-18.

Atienza et al. Mechanism of fractionated electrograms formation in the posterior left atrium during paroxysmal atrial fibrillation in humans. *J Am Coll Cardiol.* 2011; 57:1081-1092.

Atienza et al. Real-time dominant frequency mapping and ablation of dominant frequency sites in atrial fibrillation with left-to-right frequency gradients predicts long-term maintenance of sinus rhythm. *Heart Rhythm* 2009; 6:33-40.

Brooks et al. Outcomes of long-standing persistent atrial fibrillation ablation: a systematic review. *Heart Rhythm,* 2010; 7:835-846.

Chou et al. Epicardial ablation of rotors suppresses inducibility of acetylcholine-induced atrial fibrillation left pulmonary vein-left atrium preparations in beagle heart failure model. *J Am Coll Cardiol.* 2011; 58;158-166.

Davidenko et al. Sustained vortex-like waves in normal isolated ventricular muscle. *Proc Natl Acad Sci USA* 1990; 87:8785-8789.

Dixit et al. Catheter ablation for persistent atrial fibrillation: Antral pulmonary vein isolation and elimination of nonpulmonary vein triggers are sufficient. *Circ Arrhythm Electrophysiol.* Dec. 2012;5(6):1216-1223.

Ganesan et al. Bipolar electrogram Shannon entropy at sites of rotational activation: Implications for ablation for atrial fibrillation. *Circ Arrhythm Electrophysiol.* 2013; 6:48-57.

Gerstenfeld et al. Mapping of atrial fibrillation initiators from the thoracic veins. In: Chen SA, Hassaiguerre M, Zipes D, eds. Thoracic Vein Arrhythmias: Mechanisms and Treatment. Malden, Massachusetts: Blackwell Publishing; 2004, chapter 17, pp. 196-210.

Haïssaguerre et al. Spontaneous initiation of atrial fibrillation by ectopic beats originating in the pulmonary veins, *N Engl J Med.* 1998; 339:659-666. [PubMed: 9725923].

Issa et al. Electrophysiologic testing. In Issa ZF, Miller Jm, Zipes DP(ed): Clinical Arrhythmology and Electrophysiology: A Companion to Braunwald's Heart Disease, 1st ed. Philadelphia, Saunders Elsevier, 2009, Chapter 2, pp. 39-40.

Jalife et al. Mother rotors and fibrillatory conduction: A mechanism of atrial fibrillation. *Cardiovac Res.* 2002; 54:204-216.

Kadish et al. Vector mapping of myocardial activation. *Circulation* 1986; 74:603-615.

Krinskii V. Spread of excitation in an inhomogeneous medium (state similar to cardiac fibrillation). *Biophysics.* 1966; 11:676-683.

Lewis T. Oliver-Sharpey Lectures: On the nature of flutter and fibrillation of the auricle, *Br Med J.* 1921; 1:590-593.

Lewis T. Oliver-Sharpey Lectures: On the nature of flutter and fibrillation of the auricle, *Br Med J.* 1921; 1:551-555.

Lewis T. Observations upon flutter and fibrillation: II—The nature of auricular flutter. *Heart* 1920; 7:191-233.

Lin et al. Pulmonary vein antral isolation and nonpulmonary vein trigger ablation without additional substrate modification for treating longstanding persistent atrial fibrillation. *J Cardiovasc Electrophysiol.* 2012; 23:806-813.

Miller et al. Initial independent outcomes from focal impulse and rotor modulation ablation for atrial fibrillation: Multicenter FIRM Registry. *J Cardiovasc Electrophysiol.* 2014; 25:921-929.

Moe G. On the multiple wavelet hypothesis of atrial fibrillation. *Arch Int Pharmacodyn Ther* 1962; 140:183-188.

Narayan et al. Ablation of rotor and focal sources reduces late recurrence of atrial fibrillation compared with trigger ablation alone. *J Am Coll Cardiol* 2014; 63:1761-1768.

Narayan et al. Panoramic electrophysiological mapping but not electrogram morphology identifies stable sources for human atrial fibrillation: Stable atrial fibrillation rotors and focal sources relate poorly to fractionated electrograms. *Circ Arrhythm Electrophysiol.* 2013; 6:58-67.

Narayan et al. Focal impulse and rotor modulation ablation of sustaining rotors abruptly terminates persistent atrial fibrillation to sinus rhythm with elimination on follow-up: A video case study. *Heart Rhythm.* 2012; 9:1436-1439. [PubMed: 22465458].

Narayan et al. Clinical mapping approach to diagnose electrical rotors and focal impulse sources for human atrial fibrillation. *J Cardiovasc Electrophysiol* 2012; 23:447-454.

Oral et al. Pulmonary vein isolation for paroxysmal and persistent atrial fibrillation. *Circulation.* 2002; 105:1077-1081.

Pandit et al., Rotor and the dynamics of cardiac fibrillation. *Circ Res.* 2013; 112:849-862.

Pertsov et al. Spiral waves of excitation underlie reentrant activity in isolated cardiac muscle. *Circ Res* 1993; 72:631-650.

Rensma et al. Length of excitation wave and susceptibility to reentrant atrial arrhythmias in normal conscious dogs. *Circ. Res* 1988; 62:395-410.

Shivkumar et al. Acute termination of human atrial fibrillation by identification and catheter ablation of localized rotors and sources: First multicenter experience of focal impulse and rotor modulation (FIRM) ablation. *J Cardiovasc Electrophysiol.* 2012; 23:1277-1285. [PubMed: 23130890].

Wilber et al. Comparison of antiarrhythmic drug therapy and radiofrequency catheter ablation in patients with paroxysmal atrial fibrillation: A randomized controlled trial. *JAMA* 2010; 303:333-40.

Winfree T. When Time Breaks Down. Princeton University Press; Princeton: 1987.

Winterberg H. Studien u'ber herzflimmern. I. Uber die wirkung des N. vagus und accelerans auf das Flimmern des Herzens. Pflügers *Arch Physiol.* 1907; 117:223-256.

EPO Extended European Search Report, PCT/US2016/045483 (dated Feb. 14, 2019).

* cited by examiner

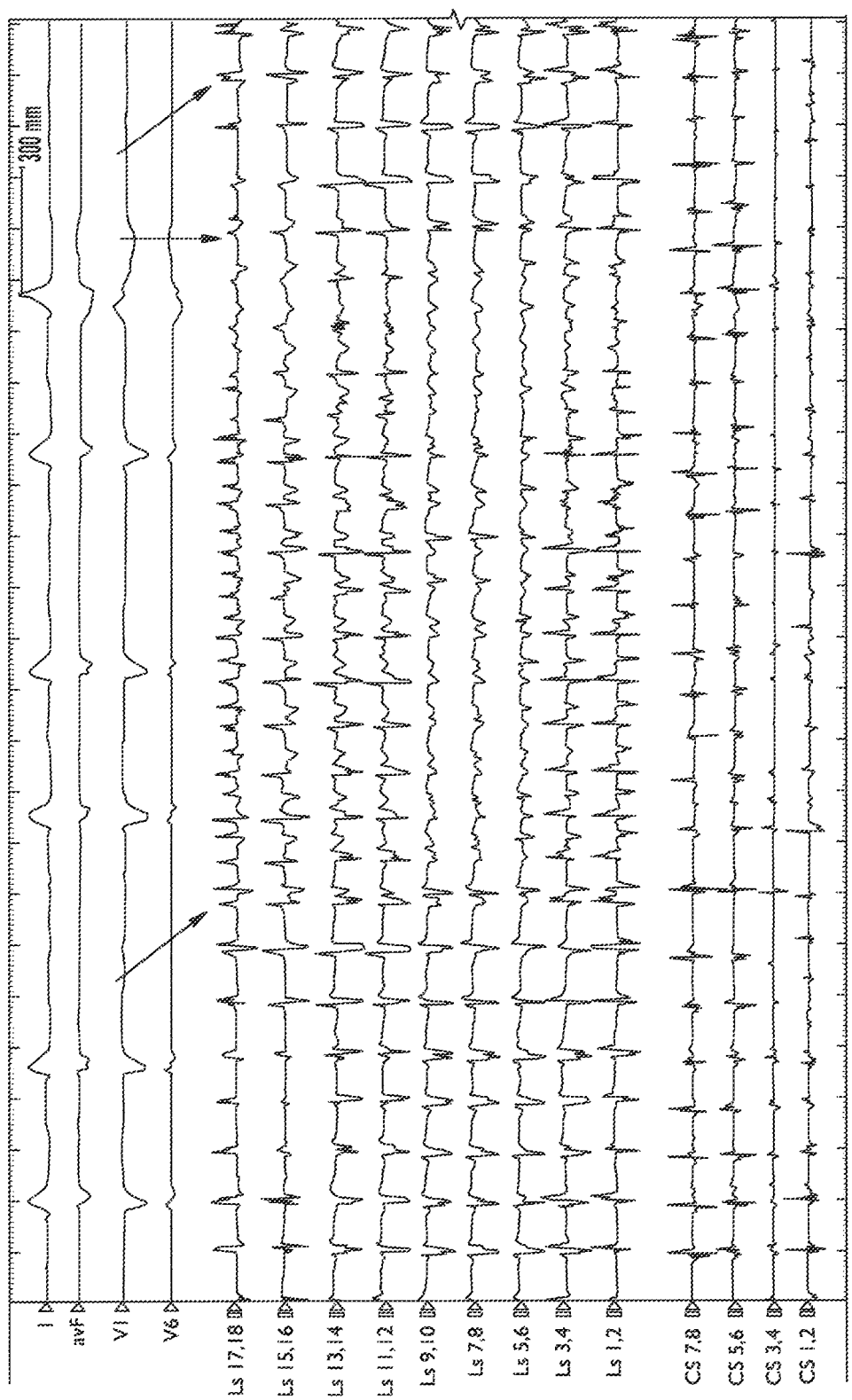

DEVICES AND METHODS FOR MAPPING CARDIAC ARRHYTHMIA

CROSS REFERENCE TO RELATED APPLICATION

This application claims filing benefit of U.S. Provisional Patent Application Ser. No. 62/201,874 having a filing date of Aug. 6, 2015, which is incorporated herein by reference in entirety for all purposes.

BACKGROUND

Atrial fibrillation is the most common cardiac arrhythmia. It creates rapid quivering of the upper chambers of the heart. Acute symptoms can include palpitations, chest pain, shortness of breath and dizziness. Prolonged arrhythmia can result in significant morbidity by potentially causing congestive heart failure and/or stroke.

Theoretical and computational cardiac models have helped to confirm that during arrhythmia the electrical wavefront transmitted through the heart causing contraction or a heartbeat degenerates into one or more rotors. Rotors exhibit a characteristic spiral-shaped wave front of depolarization from a core of affected cells. A rotor's spiral waves present as a repetitive cycle of electrical activation around the central core.

The current understanding of atrial fibrillation in humans requires a coordination of two main events. First, an initiating cardiac electrical impulse or trigger occurs elsewhere than the normal sinus node pacemaker of the heart. This trigger most commonly originates from sleeves of cardiac tissue at the opening of the pulmonary veins within the left atrium but may also emanate from non-pulmonary vein sites or even degenerate from reentrant circuits (sites from which the cause of the arrhythmia is due to the electric signal not moving in a single wave front from the atria to the ventricles as in the normal circuit, but rather as a circuit looping back upon itself). The second event is rotor formation. A rotor develops when the depolarizing electrical impulse that propagates away from a trigger in the form of a wave front undergoes a wave break, turning on an axis. The turning wave front is believed to be a result of regional changes in structure, fibrosis, fiber orientation, autonomic innervation, local conduction velocity characteristics, and/or refractory periods. The curved wave front of the rotor can create a self-sustaining circular trajectory that spins around its rotor core, called a phase singularity. A rotor can spin fairly fast, with any one rotor having a characteristic cycle length. Cycle lengths have been documented in ranges of about 130 to about 210 milliseconds and are stable over time, for instance up to tens of minutes. It has been postulated that atrial fibrillation is maintained by a small number (1-2) of high frequency rotors that drive the continuation of the atrial fibrillation. In the case of multiple simultaneous rotors, the rotor exhibiting the highest frequency is considered the driving rotor. High frequency rotors occur more frequently in the left atrium, resulting in a gradient of atrial fibrillation drivers from left to right chambers.

Treating atrial fibrillation by ablation of trigger sites and rotors has shown better results in maintaining sinus rhythm and quality of life as compared to medical therapy. Much investigation is ongoing to further improve acute success rates and longevity of being arrhythmia-free, with mapping and ablation of rotor sites being added to accepted methods of atrial fibrillation ablation.

There are currently two commercially available methods for mapping of rotors. Dominant frequency mapping involves time consuming point-by-point recording of the electrical activity within the heart. Each recording is analyzed by spectral analysis to determine each specific site's most stable dominant frequency. A site-specific recording may provide information about that point, but does not provide much information about whether a rotor is nearby. Trying to find a rotor or the path along which a rotor precesses is by hunt-and peck without any guidance as to where to try next.

The second method uses a basket catheter to record electrical activity simultaneously from 64 electrodes (8 electrodes over each of 8 splines). The simultaneous local electrical activity of the atrial chamber is displayed panoramically in 2 dimensions. Recording by basket catheters also presents challenges. Stable electrode contact can be problematic but is required to record, compute and display cardiac electrical activity. Unfortunately, many patients with persistent forms of atrial fibrillation have enlarged atria that can be significantly larger than the basket itself. This results in the substantial technical limitation of not having adequate tissue contact for many of the electrodes. In addition, electrode spacing ranges between 4 to 8 mm along splines, depending on basket size, and full expansion of the largest basket catheter to a diameter of 6 cm results in electrode separation between splines of about 2.5 centimeters. Rotor diameters are estimated to be about 1.5 cm to 2 cm. Thus, the basket geometry allows for only one or two at most electrodes on the catheter to record within a rotor site. The consequential wider spline separation of basket catheters in these enlarged atria diminishes the probability to accurately identify a rotor location.

What are needed in the art are devices and methods for mapping cardiac tissue and thereby recognizing locations of interest during cardiac arrhythmia. For instance, improved ability to map, identify and ablate rotors would be of great benefit. Presently, a rotor site cannot be identified by standard recording techniques and requires color activation time maps. A device and method that can provide for immediate rotor detector/locator, an ectopic site detector/locator and a circuit locator would be of great benefit.

SUMMARY

According to one embodiment, disclosed is a method for mapping cardiac tissue. A method can include placing an array of electrodes in contact with cardiac tissue. The method can also include obtaining electrical signals from a plurality of bipolar electrode pairs of the array (e.g., at least two bipolar electrode pairs), with each bipolar electrode pair including a first electrode and a second electrode. The first and second electrodes of each bipolar electrode pair are at a distance from one another and in electrical communication with one another. The bipolar electrode pairs are located with respect to one another such that the individual electrodes of the bipolar electrode pairs together define a perimeter around an area. The first and second electrodes of each bipolar electrode pair are located on this perimeter such that they are opposed to one another across this area. For instance, in one embodiment, the electrodes of the bipolar electrode pairs together define a circular perimeter. In this embodiment, the first and second electrodes of each bipolar electrode pair can be diametrically opposed to one another across the circular pattern.

A method can also include analyzing the electrical signals from each of the bipolar electrode pairs to determine the direction or source of a wave front of depolarization passing through the cardiac tissue. In one particular embodiment, the method can determine the precessing direction and/or core location of a rotor.

In one embodiment, a method can include unipolar analysis of the electrical signals of catheter electrodes. Through unipolar analysis of the signals from each electrode sequentially around the perimeter of a catheter area, information regarding the location of a rotor core can be obtained. For instance, through analysis of the electrical signals from bipolar electrode pairs, one can determine the precession direction of the rotor and that a rotor core is within an area defined by the electrodes. Following this determination, unipolar analysis of the signals from the electrodes around the perimeter of the area defined by the catheter can be carried out to provide additional information regarding more specific location of the rotor core within the area defined by the perimeter.

According to another embodiment, disclosed is a cardiac mapping catheter that includes an array of electrodes, the array including a plurality of bipolar electrode pairs. The bipolar electrode pairs can be located with respect to one another such that the electrodes of the bipolar electrode pairs together define a perimeter surrounding an area. The first and second electrodes of each bipolar electrode pair can be opposed to one another across this area. For example, the array can be carried on one or more circular turns of a flexible coil-type catheter with the first and second electrodes of each bipolar electrode pair being diametrically opposed across a circular turn of the coil-type catheter. In other embodiments, the array of electrodes can be carried on a basket-type catheter or on any other sort of a network that includes a grid of electrodes the signals of at least a portion of which can be measured as a plurality of bipolar electrode pairs surrounding an area as described.

BRIEF DESCRIPTION OF THE DRAWINGS

The present disclosure may be better understood with reference to the following figures:

FIG. 11 illustrates recordings from electrocardiogram surface leads including recordings from diametrically opposed bipolar electrode pairs as described herein.

DETAILED DESCRIPTION

Figure 1:
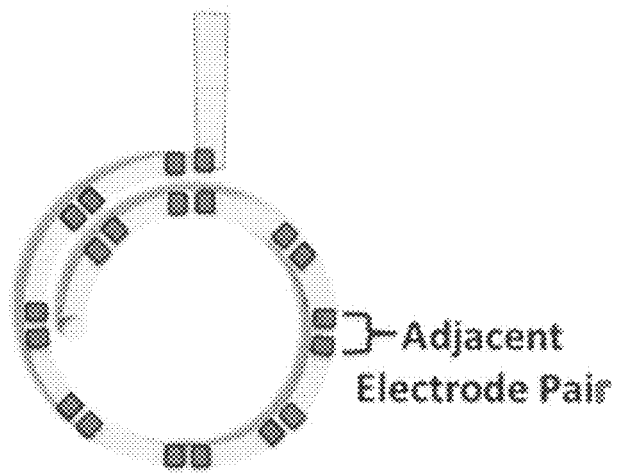
FIG. 1 schematically illustrates a prior art circular mapping electrode catheter.

It is to be understood by one of ordinary skill in the art that the present discussion is a description of exemplary embodiments only, and is not intended as limiting the broader aspects of the present invention.

The present disclosure is generally directed to devices and methods for mapping cardiac tissue. More specifically, disclosed methods and devices can be utilized to detect the direction and/or source of a depolarization wave front associated with cardiac arrhythmia. For instance, by use of the disclosed methods and devices, a rotor source location can be identified. Following identification and mapping, the rotor source can be ablated, leading to decrease in arrhythmic episodes and longevity for arrhythmia-free periods.

A mapping catheter as disclosed herein includes a plurality of bipolar electrode pairs (at least two bipolar electrode pairs) in an electrode array. Each bipolar electrode pair includes a first and second electrode. The bipolar electrode pairs of the array are located with respect to one another such that the individual electrodes of the pairs together define a perimeter, e.g., a circle, an oval, or any other perimeter. In addition, the first and second electrodes of each bipolar electrode pair can be located such that they are opposed to one another across the area that is surrounded by the perimeter (also referred to herein as the central area). For instance, in one embodiment, the electrodes of the bipolar electrode pairs can together define a circular pattern. In this embodiment, each member of each bipolar electrode pair can be diametrically opposed to one another across the area that is surrounded by the circular perimeter.

It should be understood that while much of the following discussion is directed to a circular perimeter defined by the electrodes of the bipolar electrode pairs, the disclosed methods and devices are in no way limited to circular perimeters, and the electrodes of the bipolar electrode pairs can together define any perimeter shape including circular, elliptical, ovoid, a perimeter with no clearly defined shape, or any other shape. The perimeter can define an enclosed area and this area can include a center that is equidistant from opposing points on the perimeter. For instance, with regard to a circle or an ellipse, the central area can include the center point of the area surrounded by the perimeter.

The opposing arrangement of the bipolar electrodes can be utilized during vector analysis of the electrical signals to identify directional paths of moving electric fields or wave fronts in any direction passing across the endocardial surface.

Bipolar and/or unipolar analysis of the signals from electrodes arranged as disclosed herein can be utilized to provide data concerning a depolarization source. For instance, a combination of both bipolar and unipolar signal analysis can provide a method to track a rotor and to not only identify the specific location at a point in time but also to track local movement (precession) of the rotor through heart tissue in real time. The bipolar data can identify the direction by which a rotor may approach and/or leave a catheter perimeter area. The bipolar data can identify the time at which the rotor has crossed into the area circumscribed by the catheter (or electrode perimeter shape) according to a change in the pattern of signals as described further herein. Upon determination that the rotor is within the circumscribed recording area, unipolar data can then be used to confirm this relative position, and by geometric analysis the position of the rotor core within the area can be pinpointed with each subsequent revolution.

In one particular embodiment, multiple simultaneous adjacent areas can be examined, and a rotor can be tracked as it passes from one recording area into the next, providing a continuous tracking of rotor motion. Such information may be useful to eliminate potential paths that a rotor can utilize to maintain its existence.

Beneficially, through analysis of the wave front vector, the catheters can be used to identify source locations as well as types of triggers and/or drivers of cardiac arrhythmia. In one particular embodiment, the catheters can be utilized to identify rotors, but it should be understood that the catheters are not limited to rotor identification/description. A catheter can be utilized to identify location and type of ectopic trigger foci and/or to delineate reentrant pathways that frequently complicate atrial fibrillation ablation.

A catheter can be utilized to differentiate types of arrhythmia triggers and drivers. For instance, by use of a catheter as disclosed herein, different types of rotors can be categorized. In addition, the general location tendencies or rotors and rotor types can be determined. With regard to examination of individual rotors, a variety of characteristics including but not limited to rotational speed, rotational direction (clockwise or counter clockwise), precess direction and precess velocity can be examined. The individual characteristics of a rotor once determined can be compared and contrasted with those of other rotors in the individual as well as with chronicity of atrial fibrillation, information that can be used to better identify preferred treatment options for a patient.

A catheter including a circular pattern of electrodes as described herein can be relatively small and thus less invasive as compared to previously known heart catheters. This can also provide ease in mobility and position adjustment during use, which can reduce mapping time of the cardiac tissue. Reduced mapping time can reduce radiation exposure to patients as well as require less processing time and memory of the catheter system, both of which provide great benefit.

In one embodiment, the catheter can also be utilized as an ablation catheter. In any case, following identification and classification of the components of complex atrial arrhythmia in a patient a protocol can include targeted ablation of the identified locations, e.g., rotors, ectopic foci and/or reentrant circuits. For instance, following use of a catheter to map the cardiac tissue and identify ectopic triggers, rotor core sources, etc. the catheter can be adjusted as necessary and the targeted tissue can be ablated via, e.g., radio frequency energization of electrodes of the array.

As illustrated in FIG. 1, the electrode arrangement of a typical prior art circular mapping catheter includes 10 bipolar electrode pairs (20 electrodes total). Each bipolar electrode pair includes two immediately adjacent electrodes with narrow spacing between the two. For instance, the spacing between the two electrodes of one bipolar electrode pair is generally about 2 millimeters and the spacing between successive bipolar electrode pairs is generally about 5 millimeters. During use, the voltage potential difference between the individual members of a pair is recorded. As known, a rotor exhibits a stable cyclic pattern of a short electrical impulse followed by quiescence. If one of the electrodes of a bipolar electrode pair of a standard catheter as shown in FIG. 1 is within the rotor region, then the regular pattern of electrical activity may be seen but little or no information with regard to the rotor motion (e.g., rotational direction, precession direction) or rotor core location will be obtained.

Figure 2:
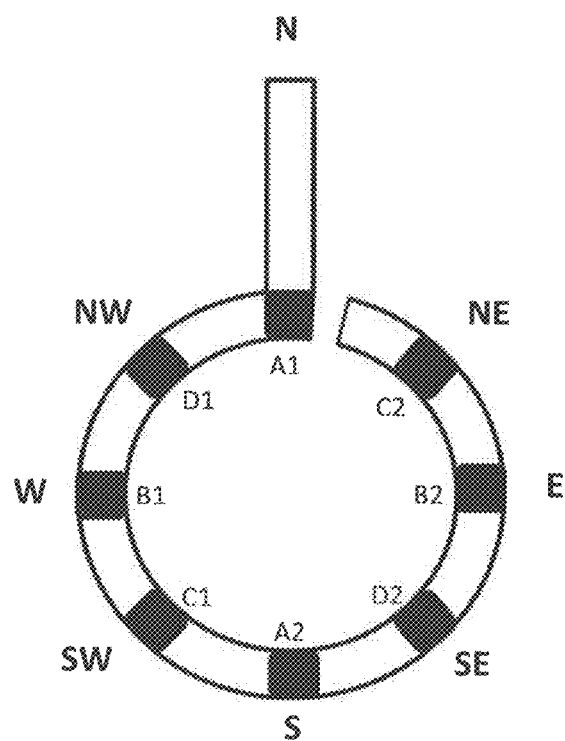
FIG. 2 schematically illustrates one embodiment of a circular mapping electrode catheter as described herein.

FIG. 2 illustrates one embodiment of a circular mapping catheter utilizing an array of bipolar electrode pairs as disclosed herein. In this embodiment, the array of the catheter includes four bipolar electrode pairs (eight electrodes), but it should be understood that an array can include two, three, or more bipolar electrode pairs. In addition, and as described further herein, all or only a portion of the electrodes of an array can be utilized at any one time as the plurality of bipolar electrode pairs that together define a perimeter.

The electrodes of each bipolar electrode pair are in electrical communication with one another and also with processing equipment according to standard practice to form leads that can detect and record the voltage potential difference between members of each pair. In accord with known signal processing techniques, one electrode of the pair is designated as the positive input and the voltage potential of the other member of the pair (the negative input) is subtracted from the voltage potential of the positive input to yield the bipolar potential of the pair. Electrical signal processing equipment, e.g., operational amplifiers, resistors, capacitors, etc. can be utilized according to standard practice to obtain the bipolar potential of each pair with the desired polarity.

Referring again to FIG. 2, the electrode array includes 8 electrodes in electrical connection with one another so as to form 4 bipolar electrode pairs. The 8 electrodes together define a perimeter (in this case a circle), with the members of each pair opposed to one another across the center of the perimeter. As shown in FIG. 2, the electrode array includes a first bipolar electrode pair (A1, A2), a second bipolar electrode pair (B1, B2), a third bipolar electrode pair (C1, C2) and a fourth bipolar electrode pair (D1, D2). Note on FIG. 2 that the electrodes of each pair are separated around the circle, with a first electrode of a pair (e.g., A1) across the circle from the second electrode of that pair (A2), and thus diametrically opposed from its mate. For ease of reference, the pairs can be configured to cardinal positions around the circle like a compass. Thus, upon location of electrodes and an array in contact with cardiac tissue, vector analysis of an electrical wave front recorded by the four bipolar electrode pairs can provide directional information regarding approaching wave fronts from a north (N), south (S), east (E), west (W), northeast (NE), northwest (NW), southeast (SE), and southwest (SW) direction, as shown.

In the illustrated embodiment, the north electrode A1 of the north/south electrode pair A1, A2 is designated as the electrode position at the top of the circular mapping catheter where the stem shaft of the catheter turns to form the circle portion of the catheter. The cardinal direction positions of a set of bipolar electrode pairs carried on a catheter can then be located around the circle by viewing the circle from the position of the shaft. These cardinal points can be utilized to refer to electrode positions for ease of use for mapping and movement of the catheter. Of course, the compass references are for geometric descriptive purposes only and are not related in any fashion to geographic compass points.

The opposed electrodes of a bipolar electrode pair can be separated from one another by a distance of about 1.5 centimeters or more (e.g., from about 2 cm to about 4 cm in some embodiments), which can be equivalent to the diameter of a circular pattern of the electrodes. For instance, if 8-10 pairs of diametrically opposed bipolar electrodes surround the perimeter a circle with a 2 cm diameter, then this provides about a 10-fold improvement of the electrode density over the same size region of tissue as compared to previously known basket catheters.

Figure 3:
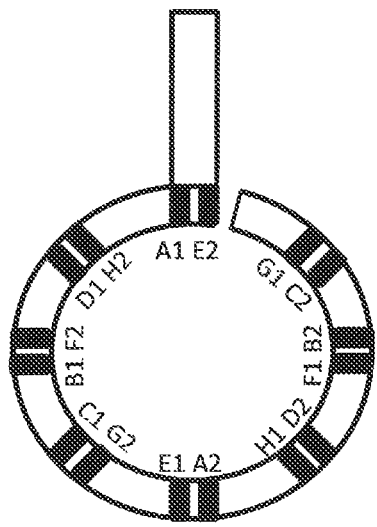
FIG. 3 schematically illustrates another embodiment of a circular mapping electrode catheter as described herein.

The electrodes to be utilized at any one time are not limited to 4 bipolar electrode pairs and a system can incorporate additional bipolar electrode pairs. For instance, FIG. 3 illustrates one embodiment of an electrode array including 8 bipolar electrode pairs (16 electrodes). The electrodes of the catheter of FIG. 3 are mated in bipolar electrode pairs as described above, i.e., A1, A2; B1, B2; C1, C2; . . . H1, H2. In this embodiment, each bipolar electrode pair is associated with another bipolar electrode pair to form an inverse input pair of bipolar electrodes. An inverse input pair includes two bipolar electrodes and thus four individual electrodes. Two bipolar electrode pairs that are associated with one another to form an inverse input pair have positive and negative inputs on opposite sides of the perimeter. As such, the signals obtained from the two bipolar electrode pairs will have an opposite initial slope, i.e., one of the bipolar electrode pairs will register a passing wave front with a first slope (e.g., positive) and the other bipolar electrode pair of the inverse input pair will register the same wave front with a second slope that is the inverse of the first slope (e.g., negative). Each electrode of an inverse input pair of bipolar electrodes is located adjacent to and at a relatively short distance from an electrode of the associated bipolar electrode pair, with the positive input electrode of the first bipolar electrode pair adjacent to the negative input electrode the second bipolar electrode pair. Thus, the positive input electrode and the negative input electrode of one of the bipolar electrodes is reversed across the perimeter as compared to the positive input electrode and negative input electrode of the associated bipolar electrode.

By way of example and with reference to FIG. 3, a bipolar electrode pair A1, A2 is associated with another bipolar electrode pair E1, E2 to form an inverse input pair of bipolar electrodes. As shown, the electrode A1 is adjacent to and at a relatively short distance from the electrode E2 of the inverse input pair. For instance, the distance between the two can be about 5 millimeters or less, or about 3 millimeters or less in some embodiments. In some embodiments, the distance between the two can be from about 0.5 millimeters to about 2 millimeters. In the pair of electrodes A1, A2, the positive input electrode of the pair can be the A1 electrode (at the north position of the array) and the negative input electrode of the pair can be the A2 electrode (at the diametrically opposite south position of the array). In the associated bipolar electrode pair E1, E2 of the inverse input pair, the input electrode is reversed on the perimeter as compared to its associated pair. In other words, for the associated bipolar electrode pair E1, E2, the positive input electrode of the bipolar electrode pair can be the E1 electrode (at the south position of the array) and the negative input electrode of the bipolar electrode pair can be the E2 electrode (at the north position of the array). In this embodiment, the A1, A2 electrode pair can be referred to as the north electrode pair (i.e., the positive input electrode of the two at the north position) and the E1, E2 electrode pair can be referred to as the south electrode pair (i.e., the positive input electrode of the two at the south position).

The other bipolar electrode pairs around the circle pattern can be likewise associated with one another in an inverse input pair relationship. For instance the B1 electrode can be the positive input electrode for the west B1, B2 electrode pair. The B1 electrode can be adjacent to and relatively close to the F2 electrode, which is the negative input electrode of the east F1, F2 electrode pair. Likewise, the B2 electrode (the negative input electrode of the B1, B2 pair) can be adjacent to and relatively close to the F1 electrode, which is the positive input electrode of the F1, F2 pair. The B1, B2 electrode pair is thus associated with the F1, F2 electrode pair in an inverse input pair relationship. The other electrode pairs around the circular pattern are likewise associated with one another in inverse input pair relationships.

A depolarizing wave front can be detected by an inverse input pair of electrodes with opposite sloping potentials. For instance, the approaching wave front can be recorded with an initial negative sloping potential by the electrode pair for which the wave front passes the positive input electrode first and the negative input electrode second. For the associated inverse input pair, however, the same wave front will pass the negative input electrode first and the positive input electrode second. Thus, the wave front will be recorded with an initial positive sloping potential for this associated inverse input pair. While the two pairs can exhibit opposite direction in the initial sloping potential, they can exhibit essentially the same voltage potential difference magnitude.

The use of inverse input pairs of bipolar electrode pairs and the equal but opposite responses to a depolarizing wave front by the bipolar electrodes can provide can provide high confidence in the wave front characteristics determined by use of the device.

Figure 4:
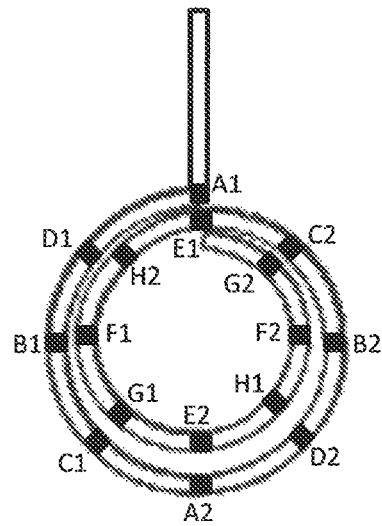
FIG. 4 schematically illustrates another embodiment of a circular mapping electrode catheter as described herein.

A circular mapping catheter can include multiple rings of bipolar electrodes as illustrated in the embodiment of FIG. 4. In this embodiment, the circular mapping catheter can include a first set of bipolar electrode pairs A1, A2; B1, B2; C1, C2; D1, D2 on an outer ring and a second set of bipolar electrode pairs E1, E2; F1, F2; G1, G2; H1, H2 on an inner ring. As shown, the inner ring can have a smaller diameter than the outer ring and as such the diametrically opposed bipolar electrodes of each pair of the inner ring can be closer to one another as compared to those of the outer ring. The use of the different sized rings can be used to improve targeting of the catheter to a particular site, e.g., a rotor core. For instance, the bipolar electrode pair of the outer ring can be initially utilized to encircle a rotor core (details of such a process are described further herein). Following location of the rotor core within the outer circle, the inner ring of electrodes can then be utilized to further narrow the location of the rotor core.

The bipolar electrodes of an electrode array can all be utilized simultaneously during a procedure. Alternatively, a portion of all available electrodes can be utilized during one portion of a procedure and optionally a second portion of all available electrodes can be utilized during a subsequent portion of a procedure. For instance, and with reference to the circular mapping electrode of FIG. 4, all of the electrodes of the inner ring and the outer ring can be utilized simultaneously during a procedure or alternatively, signals from bipolar electrodes of only the inner ring or only the outer ring can be analyzed during one portion of a procedure, with bipolar electrodes of the other ring examined during a second portion of a procedure. Of course, any combination of the multiple electrodes can be utilized during a procedure, provided that the electrodes utilized at any one time together can define a perimeter, with the individual electrodes of each bipolar electrode pair being opposed to one another across the area defined by the perimeter.

Figure 5:
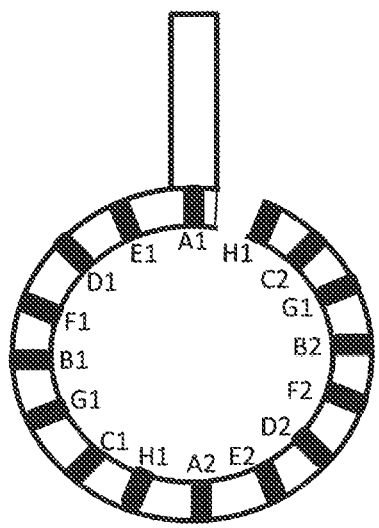
FIG. 5 schematically illustrates another embodiment of a circular mapping electrode catheter as described herein.

An electrode array can include any number of electrodes. For instance, the circular mapping catheter of FIG. 5 includes a single ring that carries 16 equally spaced electrodes in electrical communication with one another that can form 8 diametrically opposed bipolar electrode pairs. Additional bipolar electrodes included in a single ring of an electrode array can increase the detail of information obtained from the catheter during use and the mapping speed of the system. Of course, any number of bipolar electrodes can be included an electrode array and all or only a portion of the electrodes can be utilized at any one time. Moreover, an electrode array can include electrodes in addition to those that are opposed to one another to form the bipolar electrode pairs. For example, an electrode array can include one or more closely spaced pairs as found on a prior art type device as illustrated in FIG. 1. In one embodiment, an electrode array can include one or more ablation electrodes that are not members of a bipolar electrode pair. Alternatively, one or more of the electrodes of the bipolar electrode pairs can be utilized as ablation electrodes following mapping of a targeted site.

Figure 6:
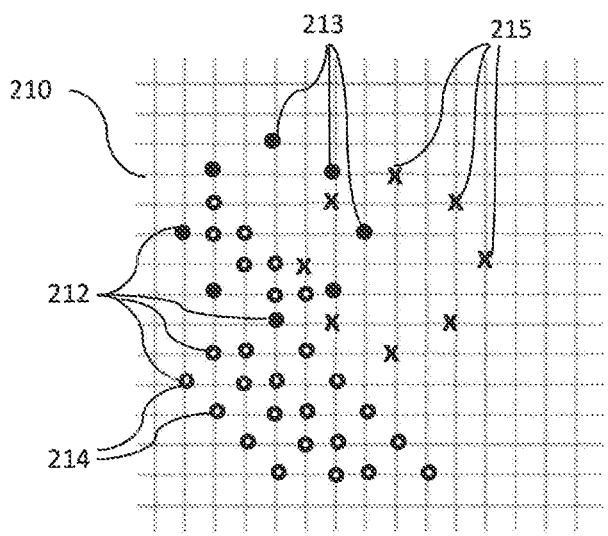
FIG. 6 schematically illustrates one embodiment of an electrode grid for use as described herein.

Any electrode array that can be utilized with a plurality of predefined bipolar electrode pairs as described is encompassed herein, and it should be understood that an electrode array is in no way to be considered to be limited to a circular mapping catheter. For instance, FIG. 6 illustrates a flexible sheet 210 that can include an array of electrodes 212 for instance in the pattern of a grid across the sheet 210. A sheet 210 including an array of electrodes 212 can include a conventional metal, for example gold, for electrical communication between individual electrodes 212. A metal electrode grid can be fabricated using known processes such as standard lithographic techniques, shadow masking, and gold deposition techniques. A sheet 210 can be of any suitable construction and material, provided the material can be utilized in a heart catheterization process. For instance, a sheet can be porous or non-porous formed of any suitable biocompatible material and can include only the electrodes 212 of the grid or can include the electrodes 212 adhered to an underlying substrate.

During use, the signals from a portion of all of the electrodes 212 of the electrode array across the sheet 210 can be measured in a mapping protocol. For instance, in the illustrated embodiment signals from the electrodes 213 marked with solid black designations can be measures while the electrodes 214 marked with open white markings are not utilized. As shown, the electrodes 213 that are utilized simultaneously in a mapping protocol define a generally circular perimeter. The electrodes 213 can be in electrical communication with one another such that there are 4 diametrically opposed bipolar electrode pairs across the circular perimeter. In one embodiment, following a period of time of mapping during which the electrodes 213 are utilized, a different set 215 of the available electrodes 212 can be utilized in a protocol. For instance, the signals from a different set of the available electrodes 215 can be measured so as to map at a different location on the sheet 210 (and thereby a different location of the contacted cardiac tissue) or so as to form a perimeter of a different size than that of the electrodes 213. Alternatively, the two sets of electrodes 213, 215 can be examined at the same time, to provide for simultaneous mapping of two different areas of the tissue. In addition, the two sets of electrodes 213, 215 can overlap with one another, as shown in FIG. 6 or can be in completely different areas of the total array, as desired.

Figure 7:
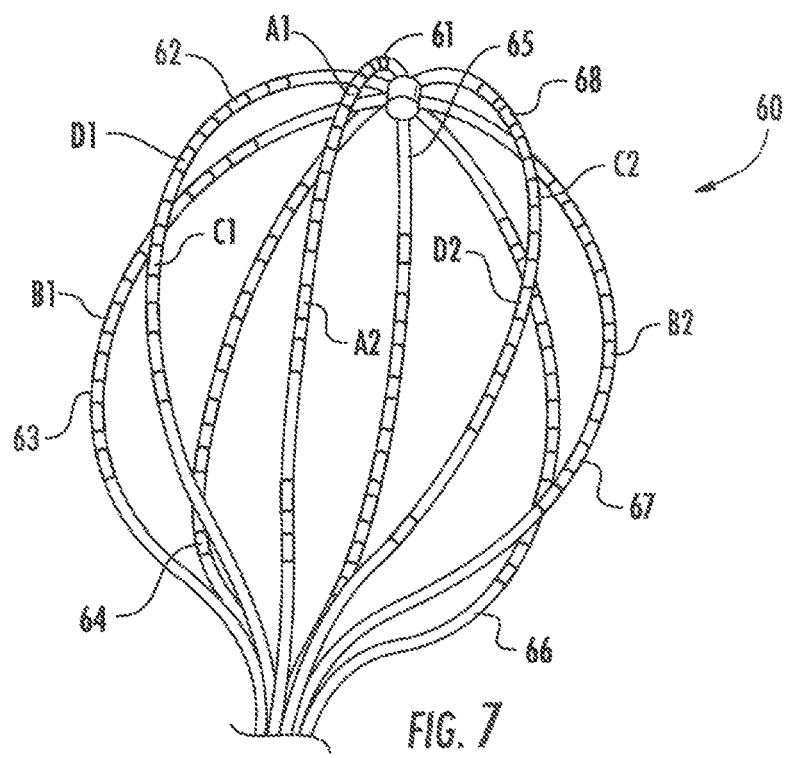
FIG. 7 schematically illustrates one embodiment of a basket-type mapping electrode catheter as described herein.

The electrode array can be of any suitable shape or design. FIG. 7 illustrates a basket-type catheter 60 that can be designed and utilized as described herein. The basket-type catheter 60 includes 8 splines 61, 62, 63, 64, 65, 66, 67, 68, each of which include 8 ring-type electrodes spaced apart along the splines. During use, a plurality of the available electrodes can be utilized that can define the multiple bipolar electrode pairs located around the desired perimeter. For instance, in the illustrated embodiment, the bipolar electrode pair A1, A2 are both located on spline 61. The bipolar electrode pair B1, B2 includes the B1 electrode on spline 63 and the B2 electrode on spline 67. The bipolar electrode pair C1, C2 and the bipolar electrode pair D1, D2 each include one electrode on spline 62 (D1 electrode and C1 electrode) and one electrode on spline 68 (D2 electrode and C2 electrode). Thus, the electrodes selected for utilization in a mapping protocol define a perimeter (A1, D1, B1, C1, A2, D2, B2, C2 around the perimeter) using electrodes on five of the available splines (61, 62, 63, 67, and 68) with the members of each bipolar electrode pair opposed to one another across the perimeter formed by the selected electrodes.

Figure 8:
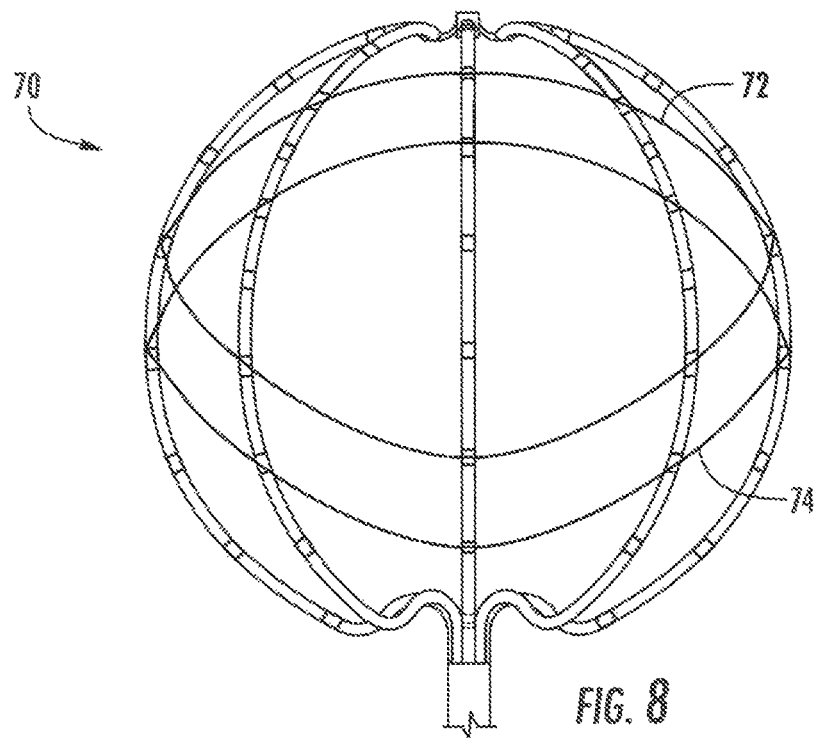
FIG. 8 schematically illustrates a method of use of a basket-type mapping electrode catheter as described herein.

Of course, any of the electrodes of a basket-type catheter can be utilized at one time. In addition, multiple different portions of all of the available electrodes can be utilized sequentially to better examine the cardiac tissue. For instance, FIG. 8 illustrates a basket-type catheter 70 that includes a plurality of splines, similar to the basket-type catheter of FIG. 7. According to one embodiment, a first set of electrodes on the five illustrated splines can together define a perimeter 72; the signals of which can be measured to map all or a portion of a heart chamber. Following this procedure, signals from a second set of all of the available electrodes on the five illustrated splines can together define a perimeter 74, and the signals from these electrodes can be analyzed to map a different portion of the heart chamber. Any combination of the available electrodes can be utilized at any time, provided the selected electrodes analyzed together can define a perimeter, with the members of each bipolar electrode of the set opposed to one another across an area defined by the perimeter. Through selection and measurement/analysis of the signals of defined sets of all of the available electrodes of a larger array, highly detailed information can be obtained with regard to arrhythmia triggers and/or drivers.

In yet another embodiment, the electrodes can be designed for external use, with each of the electrodes of the array attached to predetermined location on a patient's skin. The electrodes can be located on the patient's skin so as to define a perimeter with the electrodes of each bipolar electrode pair opposed to one another across the central area of the perimeter as described above for internal use heart catheters. The external body mapping can similarly provide information with regard to location and/or direction of arrhythmia triggers and/or drivers.

There are specific physiologic characteristics of arrhythmia triggers and drivers for which the disclosed catheters can have marked advantages over previously known types of catheters. By way of example, vector analysis of the signals from bipolar electrode pairs caused by peripheral spiral wave fronts moving away from a rotor core can provide important directional information as a signal will vary depending upon the alignment of that bipolar electrode pair with the incoming electrical activation wave front. For instance, a bipolar electrode pair that is aligned parallel to the direction of the depolarizing wave front can have a broad electrogram recording of large amplitude. In comparison, a bipolar electrode pair that is aligned perpendicular to the incoming wave front can have a narrow electrogram recording of small amplitude. In such a manner, vector analysis of the signals of the bipolar electrode pairs as described can provide specific directionality of an incoming wave front. Moreover, as the electrode array can include multiple electrode pairs and each pair can provide different data concerning the characteristics of the wave front, the combined data can be more comprehensive as compared to previously known cardiac mapping systems.

During use, a catheter can be located on tissue (e.g., cardiac tissue or skin) such that the selected electrodes of the array are in electrical communication with the tissue. Upon analysis of the electrical signals at that location, if no trigger or driver characteristic recording is seen at that particular site, then a different location can be examined. For instance, and depending upon the particular nature of the catheter, the catheter can be moved to another location or alternatively the signals from a different set of electrodes of the larger array can be examined, so as to examine a different area of tissue. The process can be continued until a characteristic electrogram recording is recognized. Upon recognition of a characteristic recording, for instance an electrogram that designates a rotor core nearby, the area of tissue that is examined can be moved in the direction of the source of the wave front based upon the directional information provided by the vector analysis of the electrogram recording. For instance, the catheter can be moved or the signals of a different set of electrodes can be examined. Once the perimeter defined by the electrodes is positioned such that the core of the rotor is within the perimeter, a very specific diagnostic signal pattern can emerge. Specifically, upon location of a rotor core within the perimeter defined by the bipolar electrodes, a single wave front activation electrogram recording can exhibit alternating slopes of double potentials that can be recorded in all of the bipolar electrode pairs simultaneously (further detailed explanation below).

If a focal ectopic trigger focus is within the perimeter of the bipolar electrodes rather than a rotor core, then a different specific diagnostic electrogram can be recorded. For instance, an ectopic focal trigger site within the perimeter of the bipolar electrodes of a catheter can present electrical wave fronts in a circular centrifugal pattern. In this case, the bipolar electrode pairs around the perimeter can present similar sloping electrograms. Triggers and drivers of arrhythmia identified by use of the bipolar electrode pairs can then be sites targeted for ablation.

Figure 9A:
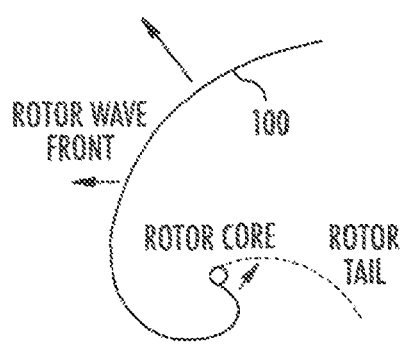
FIG. 9A-FIG. 9D schematically illustrate rotor activity in cardiac tissue and include an image of a propagating electrical wave circling around a rotor core (FIG. 9A), the rotor core outside the boundary of a circular mapping catheter (FIG. 9B), the wave front in the process of passing the circular mapping catheter (FIG. 9C), the wave front having passed the circular mapping catheter and again outside the boundary of the catheter (FIG. 9D).

FIG. 9A schematically illustrates the wave front 100 of a rotor. As shown, the rotor has a convex wave front 100 with a circular trajectory. At the core, the curvature of the wave front is highest, but the wave front cannot penetrate the core during the refractory period of the cells. Thus, the wave front activation pattern has a spiral shape.

Figure 9B:
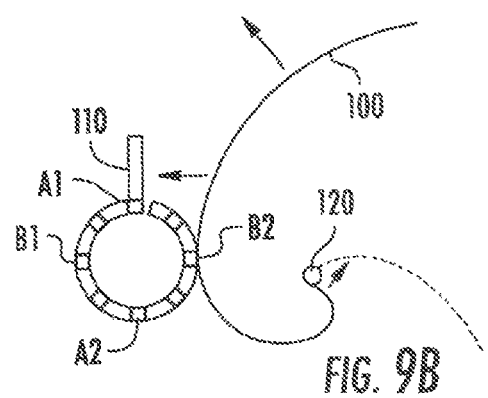
Figure 9C:
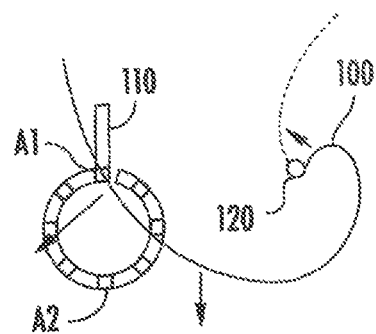
Figure 9D:
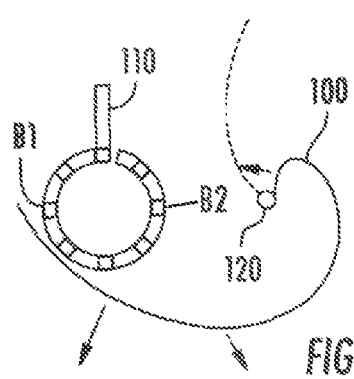

FIG. 9B, FIG. 9C, and FIG. 9D illustrate a circular mapping catheter 110 as described herein held in various relationships to a rotor wave front 100. At FIG. 9B, the rotor core 120 is outside of the diameter of the circular catheter 110. The diametrically opposed configuration of the bipolar electrode pairs provides immediate information with regard to direction of the wave front 100. For instance, in the illustrated embodiment, the earliest activated pair of the array during a rotation will be the B1, B2 pair. This pair will be essentially parallel with the incoming activation direction and will therefore have the earliest activation and largest electrogram potential amplitude. On the other hand, the A1, A2 electrodes are perpendicular to the wave front and will be the last activated of the bipolar electrode pairs of the catheter via activation of the A1 electrode as shown at FIG. 9C. The activation of the A1, A2 pair will have the narrowest smallest amplitude electrogram of all of the pairs of the catheter 110. As rotation continues, the wave front 100 passes the B1 pole of the B1, B2 pair initially encountered (FIG. 9D).

After the wave front passes, that tissue just activated is refractory from another stimulus for the duration of its refractory period. In a rotor or reentrant circuit, the wave front appears to chase its tail of refractoriness. Limiting the activation of tissue as it circles around results in very steady activation cycle lengths. The tissue near a rotor (e.g., within 1 or 2 centimeters) is driven in a 1:1 fashion with each complete rotation of the rotor, not allowing fibrillatory or more chaotic activity in that specific region. Therefore a single discreet electrogram can be recorded only with each passing wave front and with each rotation of the rotor.

Figure 10A:
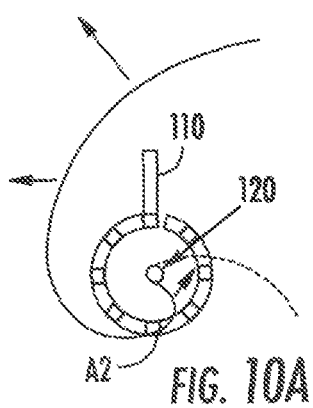
FIG. 10A-FIG. 10C illustrate a circular mapping catheter directly overlying a rotor and include an image as the wave front passes the bottom-most (or south) electrode (FIG. 10A), as the wave front passes the farthest right (or east) electrode (FIG. 10B) and as the wave front passes the top-most (or north) electrode (FIG. 10C).
Figure 10B:
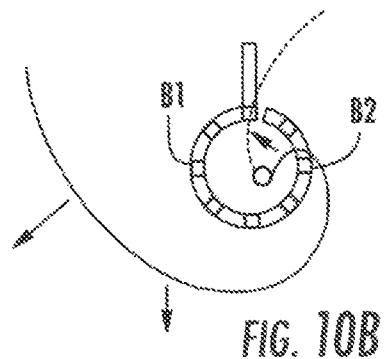
Figure 10C:
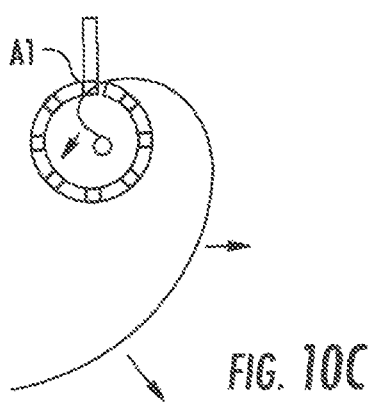

In the example illustrated in FIG. 10A-FIG. 10C, the catheter 110 is directly over a rotor core 120. Bipolar electrode recordings directly over the rotor core 120 can show secondary inverted split potentials on an electrogram. This is explained by the rotor wave front passing under one pole of a bipolar electrode pair while moving in a first direction, which results in a discreet directional slope electrogram signal, and then passing under the opposite pole, which results in an opposite slope electrogram. For instance, as the wave front passes under the A2 electrode as shown in FIG. 10A, the electrogram can exhibit a discreet upward directional slope. As shown in FIG. 10C, after the rotor turns halfway through its rotation it will pass under the A1 electrode, which is the other electrode of the A1, A2 bipolar electrode pair. During this portion of the electrogram recording, the wave front activation underneath the second A1 pole will be moving in the opposite direction as compared to when the wave front passed the A2 electrode. This will result in an inverted slope of the second electrogram potential recording as compared to the first. For instance, if the A1, A2 lead electrogram exhibited a discreet upward directional slope at the FIG. 10A orientation, the A1, A2 lead electrogram will exhibit a discreet downward directional slope at the FIG. 10C orientation. Significantly, the same inverted split potential electrogram will be recorded for all of the bipolar electrode pairs when the rotor core is within perimeter defined by the electrodes. For instance, a similar pattern will be exhibited as the wave front passes under the B1, B2 pair, the B2 pole passage being illustrated in FIG. 10B. With each single rotation of a rotor underneath a bipolar electrode pair, two distinct but opposite sloping waveforms can be recorded.

Identifying the presence of a rotor by specific rotor core characteristics with 2 to 4 millimeter electrode spacing along a linear catheter or a spline as has been previously attempted is difficult at best. Using activation wave fronts simultaneously over the entire left atrium can provide overall results but requires computational off-line assessment. Through expansion of the distance between recording bipoles and addition of more bipoles to define a perimeter in the disclosed catheters, a much larger tissue area can be examined at one time to assess for rotor activity.

In addition to the ability to map and identify triggers and drivers of atrial fibrillation, a catheter as disclosed herein can track a rotor as it precesses across cardiac tissue. FIG. 11 illustrates electrogram recordings of surface leads including diametrically opposed bipolar electrode pairs and illustrates the characteristics of a precessing rotor moving from outside the recording circle to within the circular pattern of the electrode pairs. The top 4 recordings of FIG. 11 are from electrocardiogram surface leads I, avF, V1, and V6. The next 9 recordings are from electrode pairs diametrically opposed from each other in a circular pattern. At the left-most arrow above these 9 recordings, all of these 9 tracings show a sudden transition to alternating slopes of double potential as the rotor core precesses into the circular pattern. This continues for 15 rotations. The vertical arrow marks when the rotor core precesses out of the boundary of the circular pattern and the single potential slopes resume. At the right-most arrow on FIG. 11, the rotor core has reentered the circle of diametrically opposed electrodes. The final 4 recordings at the bottom of FIG. 11 are from electrodes along a catheter located in the coronary sinus vein.

Figure 12:
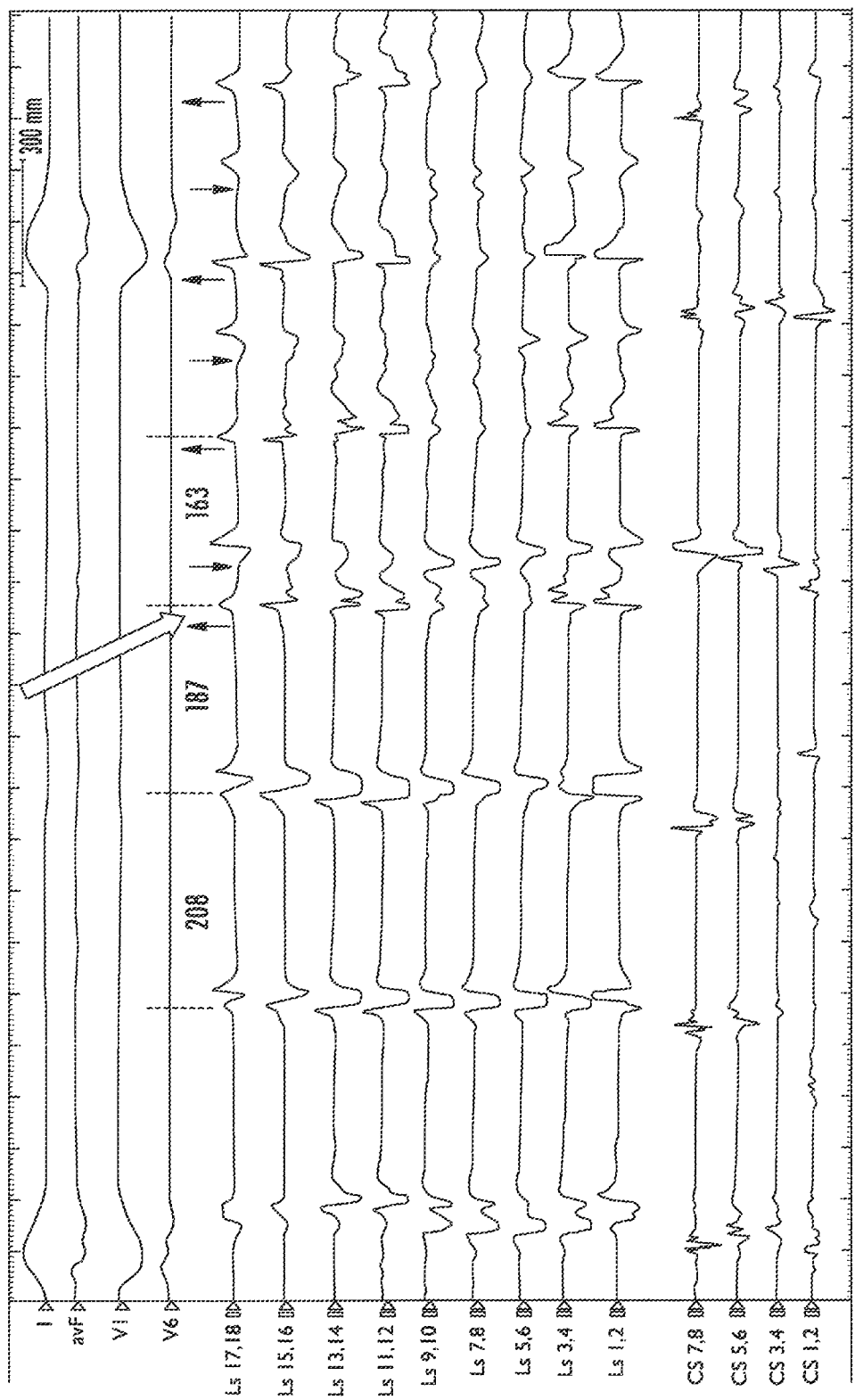
FIG. 12 illustrates recordings from electrocardiogram surface leads including recordings from diametrically opposed bipolar electrode pairs as described herein.

FIG. 12 presents another set of electrogram recordings including the top 4 from surface leads I, avF, V1, and V6; the next 9 from electrode pairs diametrically opposed from each other in a circular pattern, and the bottom 4 from electrodes along a catheter located in the coronary sinus vein. FIG. 12 illustrates how the cycle length recorded by the electrogram can be altered due to the Doppler Effect as the rotor core precesses across the cardiac tissue. As illustrated in FIG. 12, as the distance between the rotor and the bipolar electrode circle decreases, there is a decrease in cycle length. As the rotor core moves within the boundaries of the circular pattern (marked by the arrow) there is a sudden doubling of electrical potentials that alternate in slope. This is seen in all nine of the directional recordings. The rotor stays within the circular pattern for 15 rotations and then precesses back out. The pattern repeats as the rotor core precesses back and forth, in and out of the perimeter of the catheter electrodes. When the rotor is outside the circular boundary of the electrodes, the cycle length is 202 milliseconds or greater. Cycle lengths between upsloping potentials decreases to an average of 173 milliseconds when the rotor is inside the circular pattern. When the rotor migrates back out of the electrode array, the cycle length again increases (not shown on FIG. 12).

Significantly, the cycle frequency can be seen to vary by a factor of 2 (or more due to the Doppler Effect) as the rotor core precesses in and out of the perimeter defined by the bipolar electrodes. As shown in FIG. 12, when the rotor core is within the perimeter defined by the bipolar electrodes, the cycle frequency can be double or more, e.g., between 2 and 3 times, that of the cycle frequency when the rotor core is outside of the perimeter. Moreover, this effect is seen in all of the bipolar electrode signals. Thus, analysis of the signals of bipolar electrodes arranged as described can be used to quickly and definitively identify the location and direction of a rotor core as well as other features of arrhythmia.

In one embodiment, unipolar analysis of the activation signals from the electrodes defining the area perimeter can be carried out to provide information about a source of a depolarization wave front. For instance, in one embodiment, the electrode activations can be analyzed sequentially around the perimeter to provide additional information. In one embodiment, a unipolar signal analysis can be carried out following a bipolar electrode analysis as discussed above so as to provide additional information about a depolarization source. This is not a requirement of an analysis methodology, however, and in some embodiments, a unipolar signal analysis can be carried out independent of a bipolar electrode analysis.

A unipolar analysis of the electrode activation signals can be used to confirm location of a depolarization source within a predetermined area and/or to more specifically identify the location of a depolarization source (e.g., a rotor core) within the area defined by the electrodes. For instance, analysis of the bipolar electrode pair signals can initially be utilized to map from which direction a rotor approaches an area (e.g., a recording area as defined by the catheter electrodes) as well as the time and position at which the rotor crosses the perimeter into the area defined by electrodes A unipolar analysis of the electrode signals can then be carried out to locate the rotor core with higher precision. Following this analysis, the tissue at the rotor core and the paths of abnormal tissue that allow the rotor to be sustained can be treated, e.g., ablated, to decrease arrhythmic episodes. The precision mapping provided by the two-pronged analysis can prevent excessive tissue ablation and effectively treat a depolarization source with minimum tissue disruption.

Figure 13:
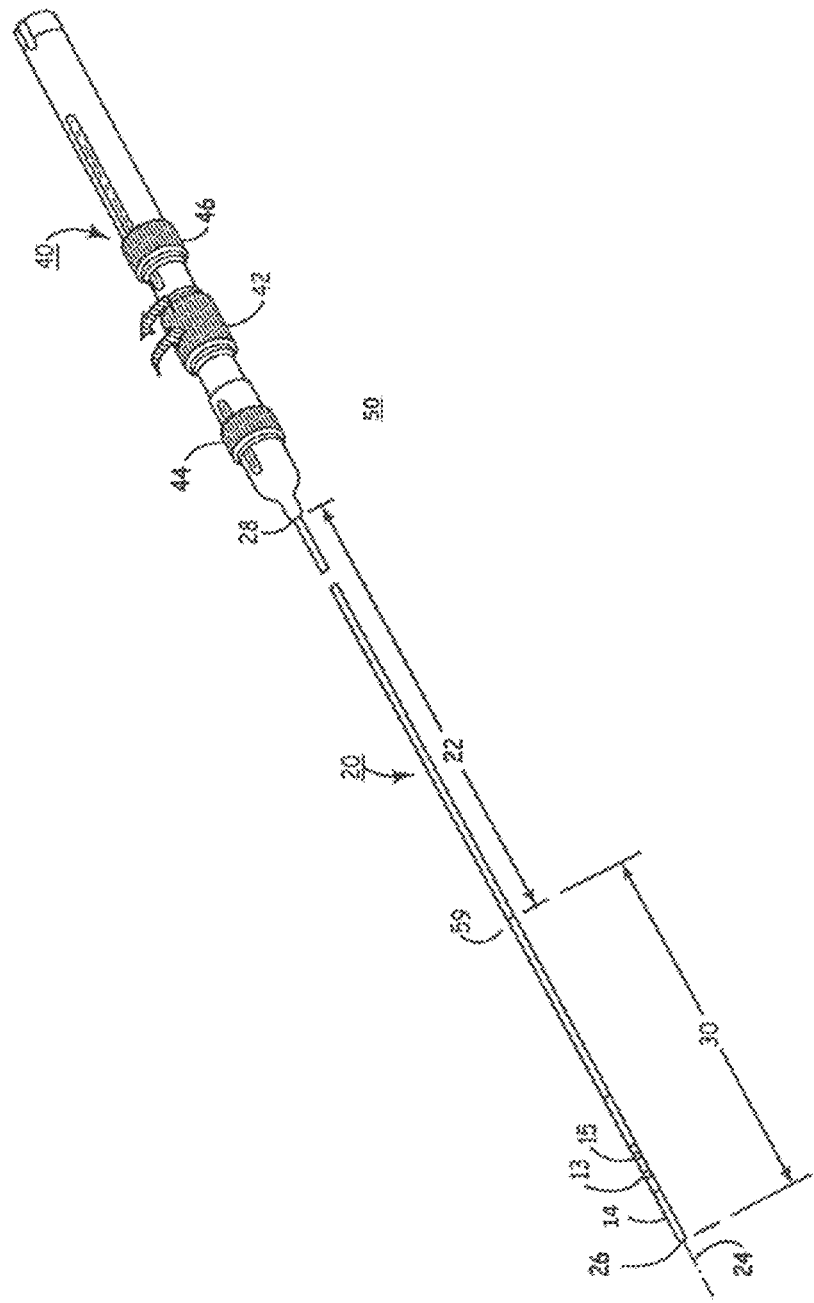
FIG. 13 illustrates three potential locations of a rotor core within a perimeter defined by a series of electrodes.

FIG. 13 schematically illustrates different possible positions of a rotor core in relation to a catheter. At position A, the rotor core is outside of the perimeter defined by the electrodes (in this particular case a circle). At position B, the rotor core is within the perimeter, and at position C, the rotor core is at the center of the circle defined by the electrodes. As the depolarizing wave front sweeps around the core as indicated by the directional arrow at rotor core position A in FIG. 13, the electrodes of the catheter will be activated in a recognizable pattern, with the pattern depending upon the relative location of the rotor core with regard to each of the electrodes of the catheter.

When a rotor core is outside of the area defined by a circular catheter, e.g., at position A of FIG. 13, the electrodes will be activated in a pattern that may not proceed sequentially around the circle. For instance, the W electrode may be activated first and followed in sequence by the NE electrode and then the E electrode, depending on the exact relationship between the rotor core and the catheter. In contrast, when the rotor core is within the perimeter, as at positions B or C of FIG. 13, the electrodes will be sequentially activated by the depolarizing wave front as is sweeps around the core. Thus, a relatively simple analysis of the order of activation of the electrodes around the perimeter of the catheter can provide information with regard to the location of the depolarization source.

Temporal unipolar electrode analysis of the activations can provide additional information with regard to the location of the depolarization source. For instance, analysis of the time gap between activation of adjacent electrodes around the perimeter can be utilized to identify the location of the rotor core as not only within or exterior to the area defined by the electrodes of the catheter, but also can provide a more precise location of the source within the area.

When a rotor core is within the area defined by the catheter perimeter, the precise location of the rotor core within the area can be determined from the time between activation of adjacent electrodes around the perimeter and the cycle length (i.e., revolution frequency) of the rotor. The cycle length of a depolarization wave front can be obtained through analysis of the repeating electrode activations at one or more of the catheter electrodes over a period of time. As discussed above, as a rotor precesses across the cardiac tissue, the cycle length at individual electrodes (either bipolar or unipolar electrodes) can exhibit a Doppler effect. However, this effect will present itself as a readily apparent variation in cycle length as the rotor precesses. Accordingly, when the cycle length as determined at a single electrode does not vary excessively over several cycles (e.g., about 10 or more cycles, for instance from about 10 to about 15 cycles), it can be assumed with high confidence that this time period corresponds closely to the cycle length of the rotor. This cycle length can be confirmed through comparison of the cycle length obtained at several different electrodes, and in one embodiment through comparison of the cycle length obtained at electrodes on opposite sides of the perimeter. When the cycle length at each catheter is stable and in correspondence with one another, this value can be assumed to be the rotor cycle length.

Figure 14:
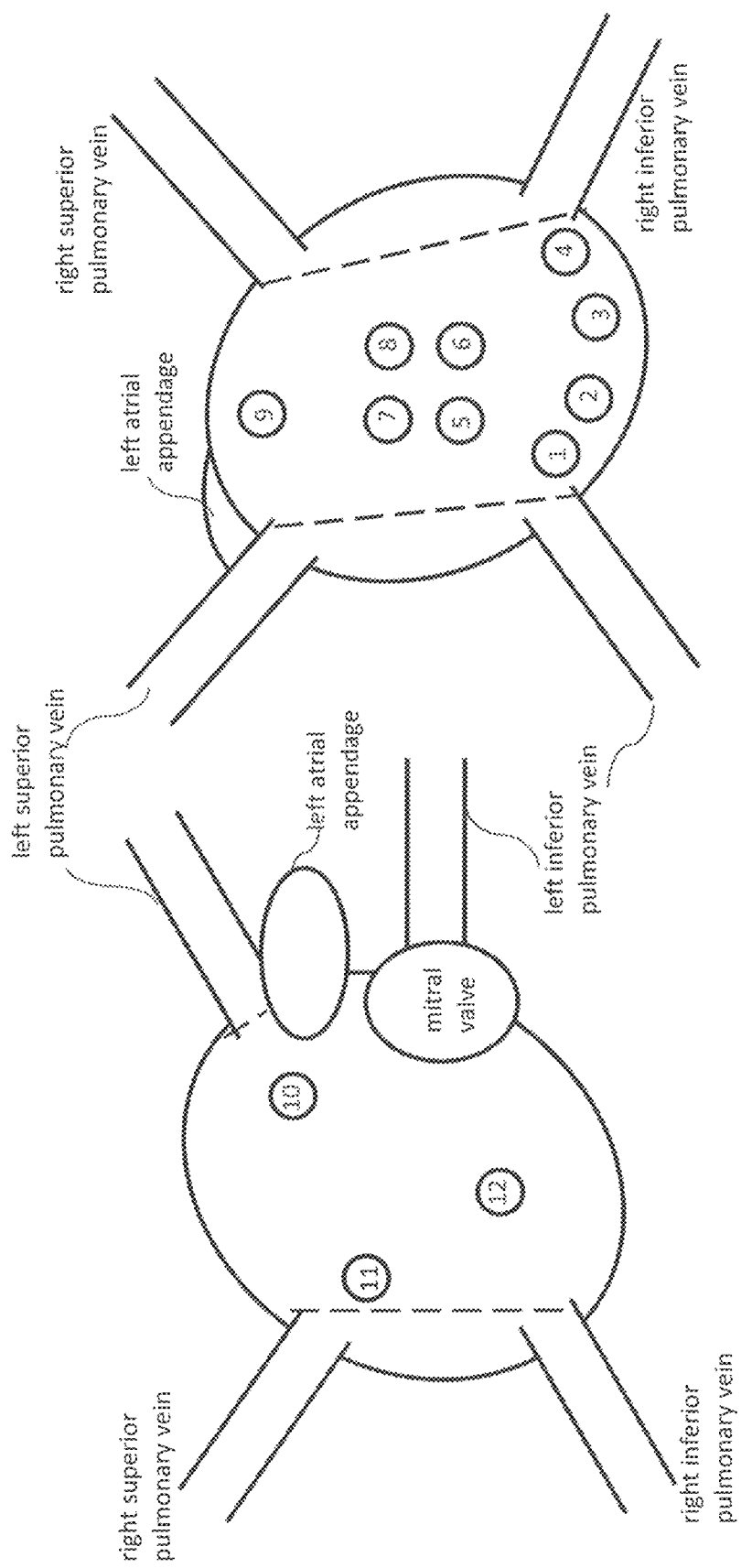
FIG. 14 illustrates a catheter and a rotor core in the center of an area defined by electrodes at the perimeter of the catheter.

FIG. 14 illustrates the special case of a rotor core located the center C of a catheter area. In this situation, the depolarizing wave front of the rotor will activate each electrode successively around the perimeter. Assuming isotropic conditions exist, and the electrodes are spaced equally around the perimeter, the time period between activations of each successive electrode will be equal to one another. For example, in the illustrated embodiment of FIG. 14, in which there are 8 electrodes equally spaced around a circular catheter area, the time gap ($t_g$) between sequential electrodes will be the rotor cycle length ($CL_{Rt}$) divided by the number of electrodes (n), or in this case, 8. If, upon analysis of the unipolar electrode activations, the time gaps are substantially equal to one another and to $CL_{Rt}/n$, then the rotor core is located at the center of the area defined by the electrodes.

Adjustments to an analysis for recognition of a rotor core under a central or other particular point of a catheter area can be carried out on a case by case basis, but are well within the capabilities of one of ordinary skill in the art. For instance, adjustments depending upon the shape of the perimeter, a differential spacing between adjacent electrodes, the particular point of the area under analysis, etc. can be carried out through geometric modeling.

Figure 15:
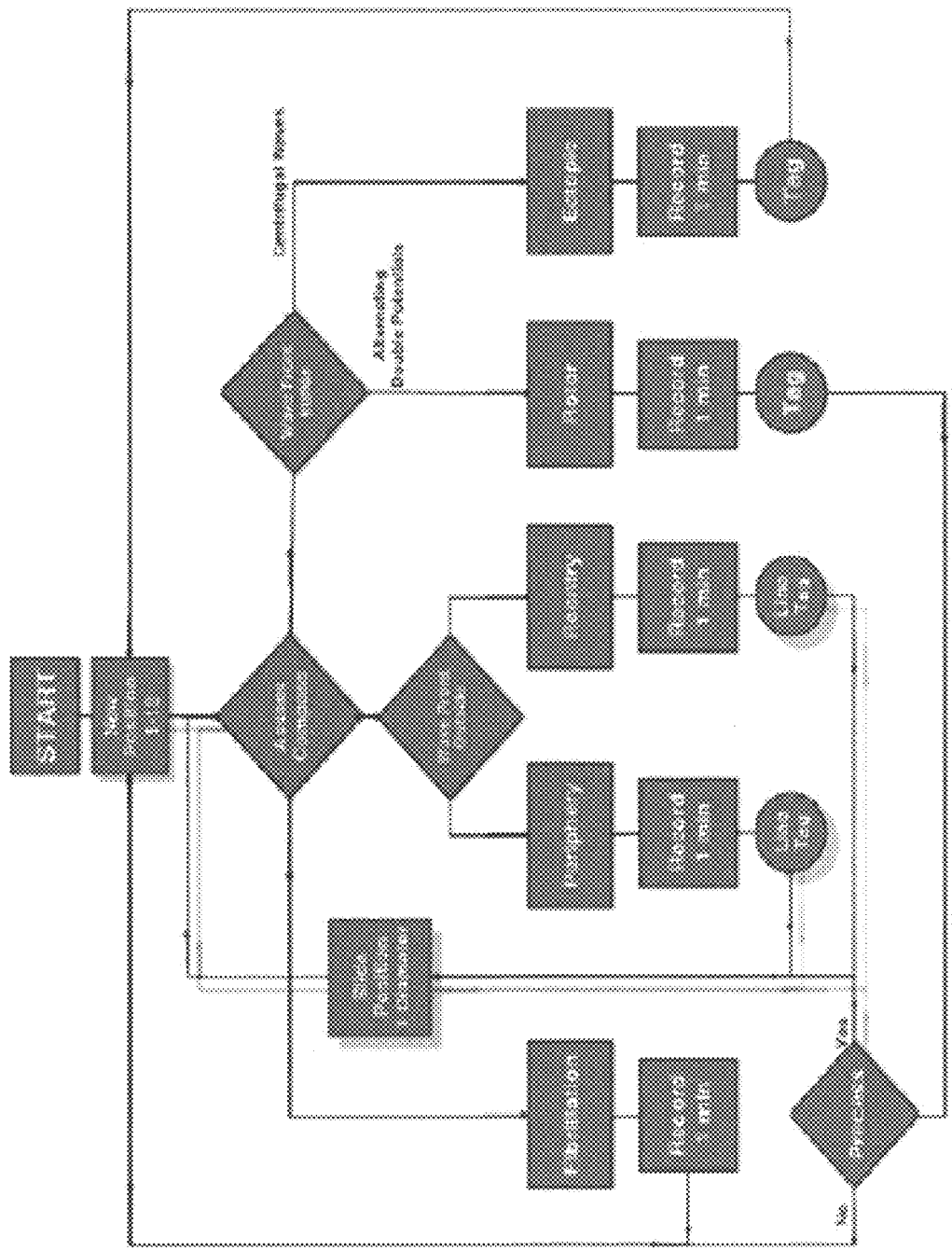
FIG. 15 illustrates a catheter and a rotor core at the periphery of an area defined by electrodes at the perimeter of the catheter.

A more general analysis can also be carried out to determine a more precise location of a rotor core within a catheter area. For instance, as illustrated in FIG. 15, a rotor core can be located on the perimeter of a catheter area and still be recognized via a bipolar analysis to be within the general catheter area. However, in this case, the rotor core can also be relatively far from the center, and ablation of the central area under the catheter may leave the rotor core area untreated.

If one assumes that a rotor spins with its lateral rotation in the same plane as the tissue surface, a general solution for determination of rotor core location within a catheter area can be determined by initial determination of the maximum possible time gap ($t_{gmax}$) between activation of adjacent electrodes, which in turn depends upon the number of electrodes located around the perimeter and the rotor cycle length $CL_{Rt}$. When a rotor is within the catheter area, the time gap between activation of adjacent electrodes around the perimeter will occur within certain time constraints. In particular, and with reference to FIG. 15, as the rotor makes one complete revolution within the area defined by the catheter perimeter, the electrodes closest to the rotor core will exhibit the longest gap time between activations (i.e., the tangential velocity of the wave front is lower closer to the rotor core). Accordingly, the maximum gap time possible for activation between adjacent electrodes will be in those instances in which the rotor core is on the perimeter and under one of the electrodes as illustrated at FIG. 15. Geometric analysis of this situation can provide a general solution for this maximum gap time in terms of the number of electrodes located around the periphery of the catheter and the cycle length of the rotor, e.g., in the case of a circular catheter:

$$t_{gmax}=CL_{Rt}(0.25+1/(2n))$$

in which $t_{gmax}$, $CL_{Rt}$ and n are as defined above.

The value obtained for $t_{gmax}$ can be utilized to confirm that the rotor core is within the catheter area. In particular, if the time gap observed between any two adjacent electrode activations is longer than the maximum time gap for the given catheter and cycle length, then the activation must be coming from a source outside of the catheter area, and the rotor core is not within the area. Conversely, if the longest observed time gap is equal to or less than the maximum possible time gap, then the rotor core is within the area that is defined by the electrodes.

Once the maximum possible time gap for a particular catheter and cycle length is determined, analysis of the actual observed time gaps between the adjacent electrodes sequentially around the perimeter of the catheter can be used to triangulate the location of the rotor core within the catheter area. For instance, the largest observed time gap between two sequential electrodes can inform the observer that the rotor is located in an angle of the tissue area defined by these two electrodes and the center of recording area. Moreover, the closer this largest observed time gap is to the maximum possible time gap as discussed above, the closer the rotor core will be to the perimeter of the catheter area.

Figure 16:
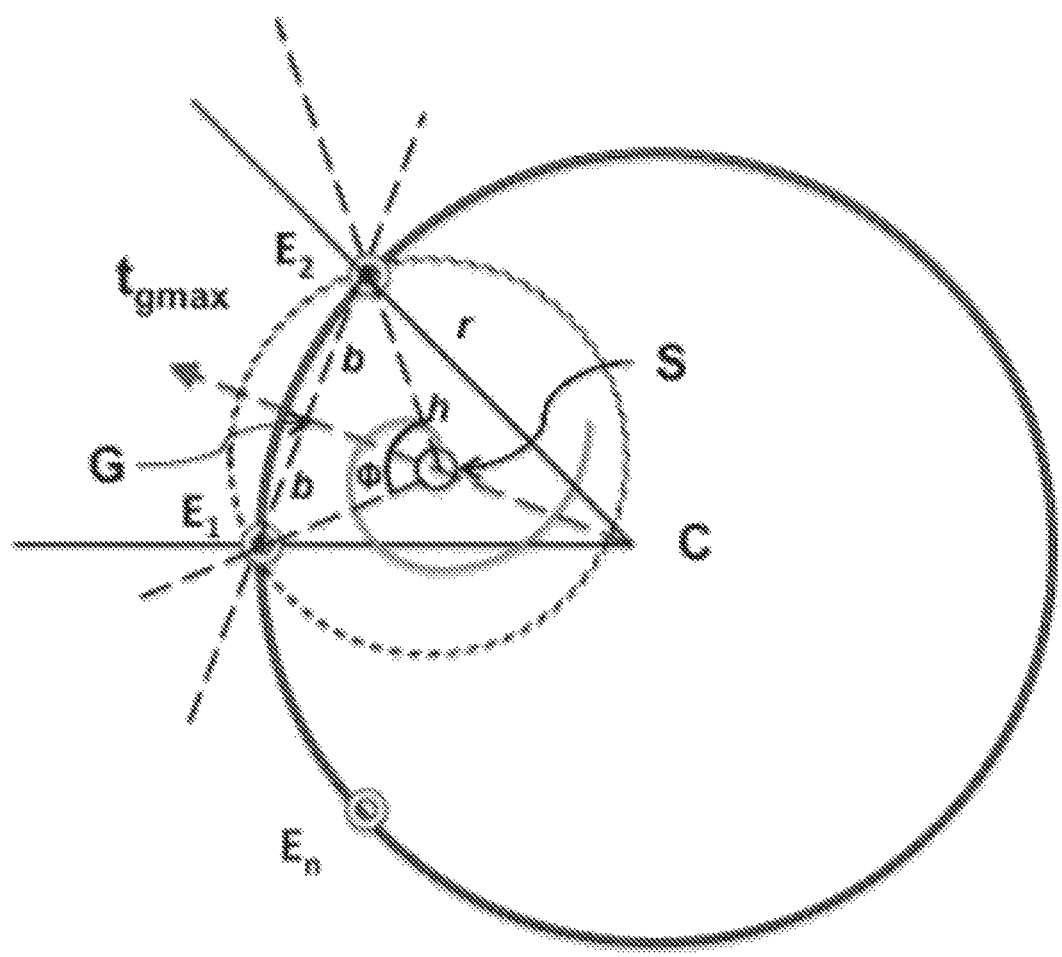
FIG. 16 illustrates one embodiment of a rotor core location within a defined perimeter and a triangulation method for determining the specific location of the rotor core by use of unipolar analysis.

FIG. 16 illustrates an example in which the rotor core (at position S on FIG. 16) is on a radius (G) that bisects an angle formed between two electrodes located ($E_1$, $E_2$) within the area of the perimeter of a circular catheter and the center (C) of the circle (i.e., the angle $E_1$, C, $E_2$ on FIG. 16). The radius length (r) of the circular catheter perimeter can be known by the catheter specifications. The maximum observed time gap would be determined as being between electrodes $E_1$ and $E_2$ upon examination of the electrode signals. The rotor core could therefore be determined to be within that angle of the circle and the rotor core can be estimated to be along or near the C-G radius. A circle (dotted circle) formed with the rotor core S at the center will have a radius h, as shown. Assuming constant rotational speed around this circle having the rotor core at the center of the circle S, $t_{omax}$ (the observed time gap between the signal at $E_1$ and $E_2$) can be considered a portion of this circle. The angle $\Phi$ is the angle formed as the wave front passes from $E_1$ to $E_2$ as described by the circle with radius h. The distance from the center of the catheter area C to the rotor core S along the radius CG will then be:

$$r(\cos(180°/n))-b \cot(\Phi/2)$$

in which r is the radius of the circle n is the number of electrodes on the perimeter b is ½ of the length of the chord ($E_1E_2$) between the two electrodes (the largest observed time gap being between these two electrodes) and $$\Phi = (t_{omax}/CL_{Rt})360°$$

Figure 17:
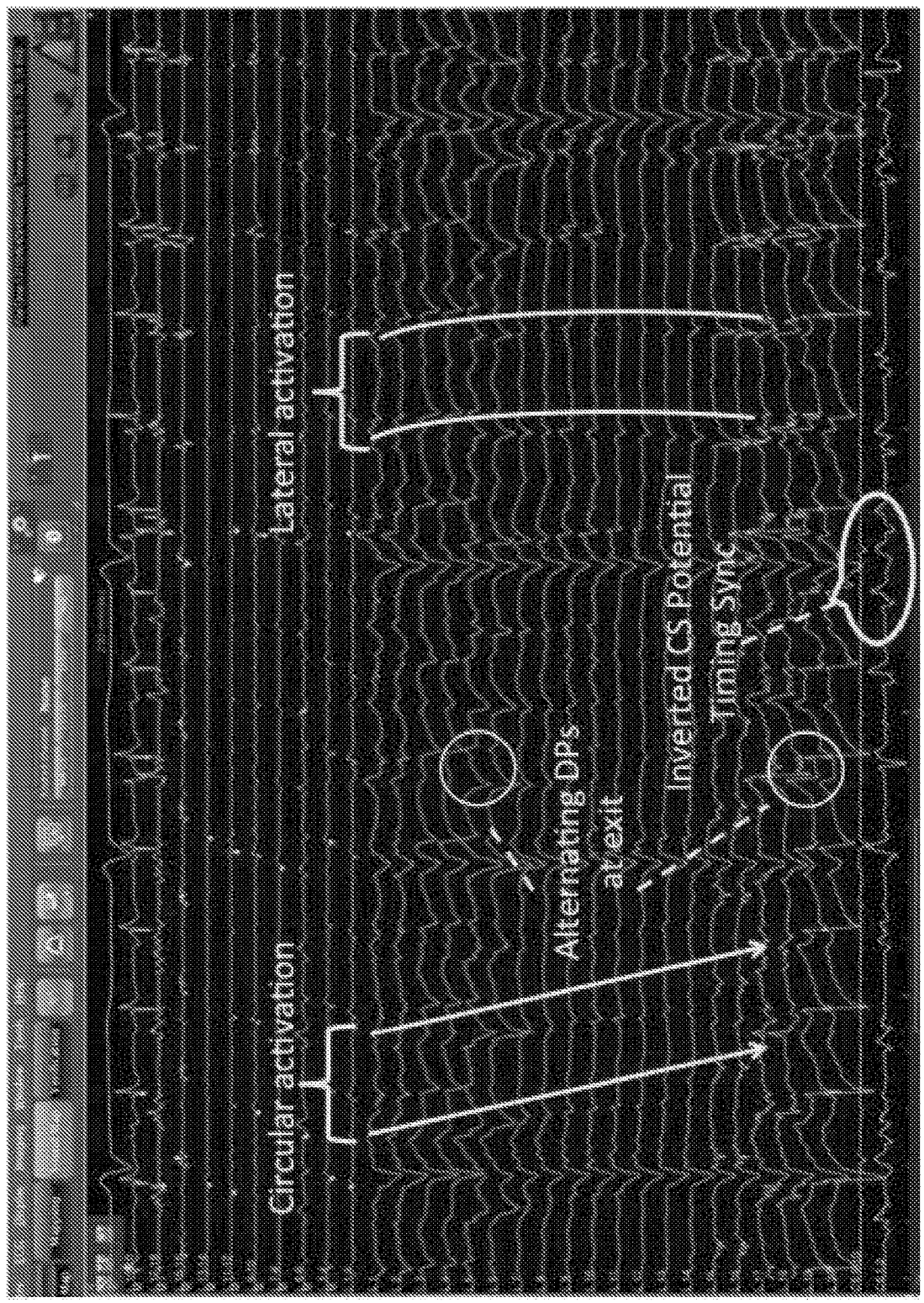
FIG. 17 illustrates recordings from electrocardiogram surface leads demonstrating unipolar electrode analysis of a rotor within the area defined by the cathode and precession out of the area.

FIG. 17 presents a set of electrogram recordings obtained from a circular catheter (similar to that illustrated in FIG. 1) that was overlying rotor activity during atrial fibrillation. This figure includes simultaneous recordings of a surface ECG, circular catheter and a coronary sinus vein catheter. The top recording in this FIG. 17 is a surface ECG recording of a patient in atrial fibrillation. The next 10 tracings are bipolar recordings of the closely paired electrograms. The next 20 tracings are the unipolar recordings of each specific electrode. The bottom 2 tracings are recordings from electrodes on a catheter that is placed in the coronary sinus vein. The left half of the figure shows rotor activity within the perimeter of the circle of electrodes 1-20. There is a cyclic pattern of sequential unipolar activation around the catheter electrodes (2 slanted arrows). The right half of FIG. 17 illustrates the rotor precessing out of the perimeter of the catheter. At the point of exit across the perimeter, the unipolar activation sequence can be seen to change to more simultaneous (2 vertical arrows).

Figure 18:
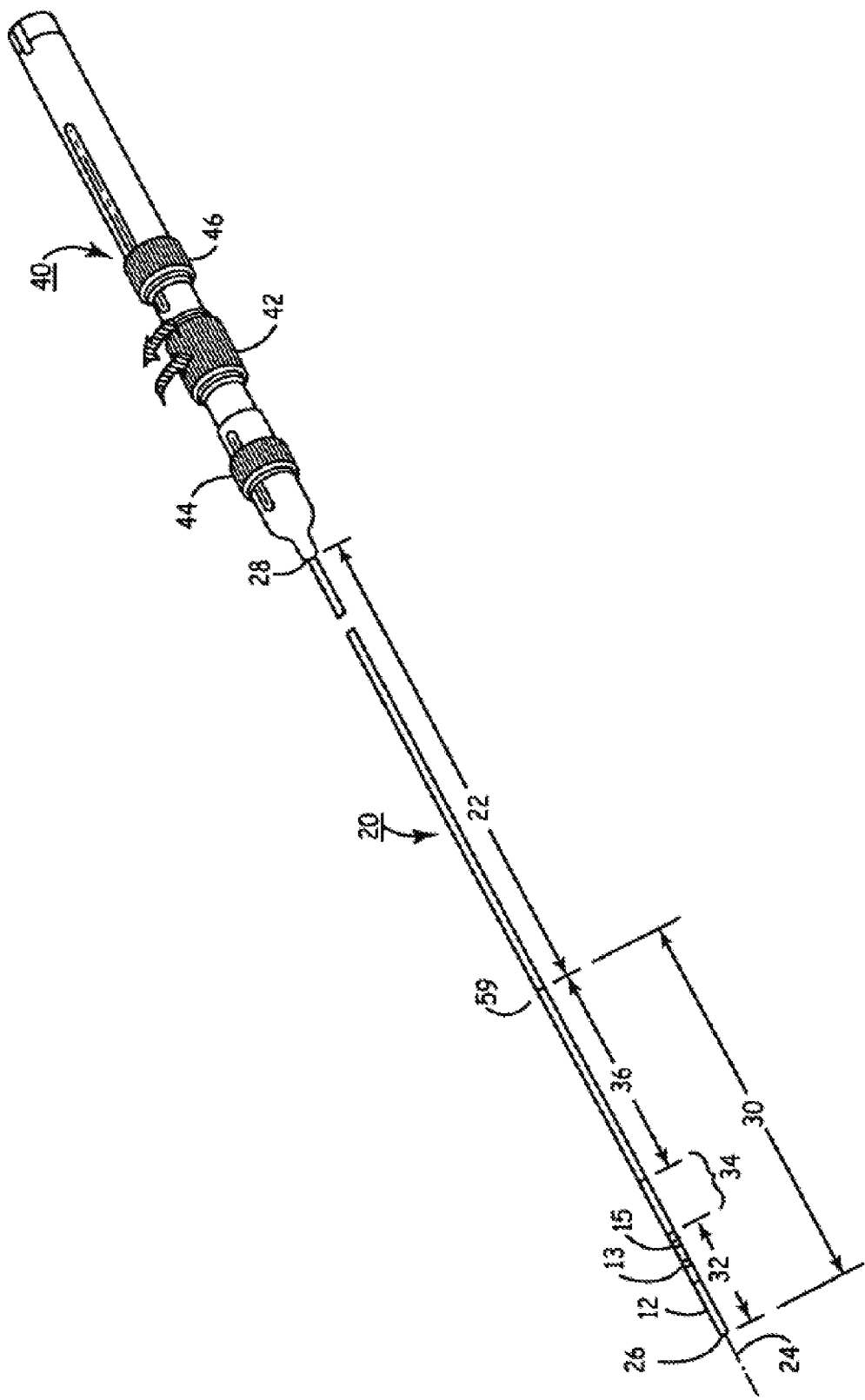
FIG. 18 illustrates one embodiment of a heart catheterization device incorporating a circular mapping catheter as disclosed herein.

An electrode array can be utilized with catheter components as are known in the art. For example, FIG. 18 schematically illustrates an anatomically-conforming, flexible catheter 50 incorporating an array of electrodes 13, 14, 15 that can be located with respect to the heart wall for mapping and in one embodiment also for ablation. The distal segment 30 is simplified in FIG. 18 to show three of the electrodes 13, 14, 15, but it should be understood that the distal segment 30 will comprise the array of at least 8 electrodes on the flexible segment that, during use, will curve to define a pattern of bipolar electrode pairs. The catheter 50 can include a porous tip and catheter lumen for emitting irrigating fluid around the electrode array as is known, but those features are not illustrated in FIG. 18 to simplify illustration. It will be understood that the catheter 50 can also function as an ablation catheter and include necessary components for delivery of ablation energy, including without limitation, visible light, infrared energy, and/or electrical energy from or along the distal tip.

The catheter 50 can include a catheter shaft or body 20 and a handle 40. The catheter shaft or body 20 can have a shaft axis 24 that extends between a distal end 26 and a proximal end 28 and can be separated into a proximal section 22 and a distal section 30. Catheter body 20 may be of any suitable diameter and length and may be straight or pre-curved along its length, but in one embodiment is straight when unrestrained. The distal section 30 or the distal segment thereof can be tapered from the diameter of the proximal section 22.

The proximal section 22 can have sufficient column strength and can be capable of good torque transmission to permit controlled placement of the distal section 30 at a target site in the heart. The distal section 30 can be deflectable away from shaft axis 24 so as to form the desired pattern during use. Each electrode 13, 14, 15 is separately connected to insulated conductors extending proximally through the catheter body 20 to terminals of a cable connector in or on the handle 40 that is connected via a cable to the mapping signal amplifiers and optionally also to an ablation energy source. A thermocouple can also be included in the distal segment 30 and separately insulated thermocouple conductors can extend proximally through the catheter body 20 to terminals of the cable connector in or on the handle 40 that are coupled to a temperature display and optionally an ablation energy control apparatus known in the art.

The handle 40 can take any of the forms known in the art for making electrical connections with the conductors within the catheter body 20 and for delivering irrigation fluid to an irrigation lumen (if present) of the catheter body 20. The handle 40 also includes a mechanism for deflecting the distal tip section 30 into a circular pattern(s) and moving the catheter within the body. The mechanism can take any form for pulling, pushing and/or twisting the deflection or push/pull wires within the catheter body 20. In the illustrated embodiment, the handle 40 is attached to the catheter body proximal end 28 and supports axially slidable manipulators comprising push-pull rings 44 and 46 and a rotatable lateral deflection ring 42 that are coupled to the proximal ends of a curve deflection push-pull wire, a knuckle deflection push-pull wire, and a lateral deflection wire. For instance, the lateral deflection ring 42 can be rotated to impart a torque in a lateral deflection wire coupled thereto to laterally rotate the distal section 30 with respect to axis 24 within the proximal section 22.

As shown in FIG. 18, when the push-pull wires are relaxed, the distal segment 30 is aligned with the shaft axis 24 which can be referenced as 0°. The knuckle deflection push-pull wire can be retracted or pulled by sliding ring 46 proximally to impart a radius bend from substantially 0° to form a circular pattern of bipolar electrode pairs of the desired diameter. The knuckle deflection push-pull wire can be extended or pushed by sliding push-pull ring 46 distally to impart a bend that is in a bend direction opposite to the bend direction imparted when the knuckle deflection push-pull wire is retracted or pulled by sliding ring 46 proximally.

The manipulator push-pull ring 44 can be moved proximally or distally to move the curve deflection push-pull wire coupled thereto proximally or distally to further affect the orientation or size of the circular pattern.

For example, pushing the push-pull ring 44 forward toward the distal tip 24 of the catheter can deflect the catheter downward in the southern direction of a circular pattern (as shown for example in FIG. 2). During use in a body, for instance when the catheter is placed against the posterior atrium wall, this movement can be translated to a more inferior position within the heart chamber. Pulling the push-pull ring 44 back can deflect the distal segment 30 in a more northern direction. When the catheter distal segment 30 is placed against the posterior wall, then a counterclockwise rotation of the catheter stem via the lateral deflection ring 42 can slide the circular mapping electrode laterally, towards the east, while a clockwise rotation moves the catheter towards the west.

Figure 19:
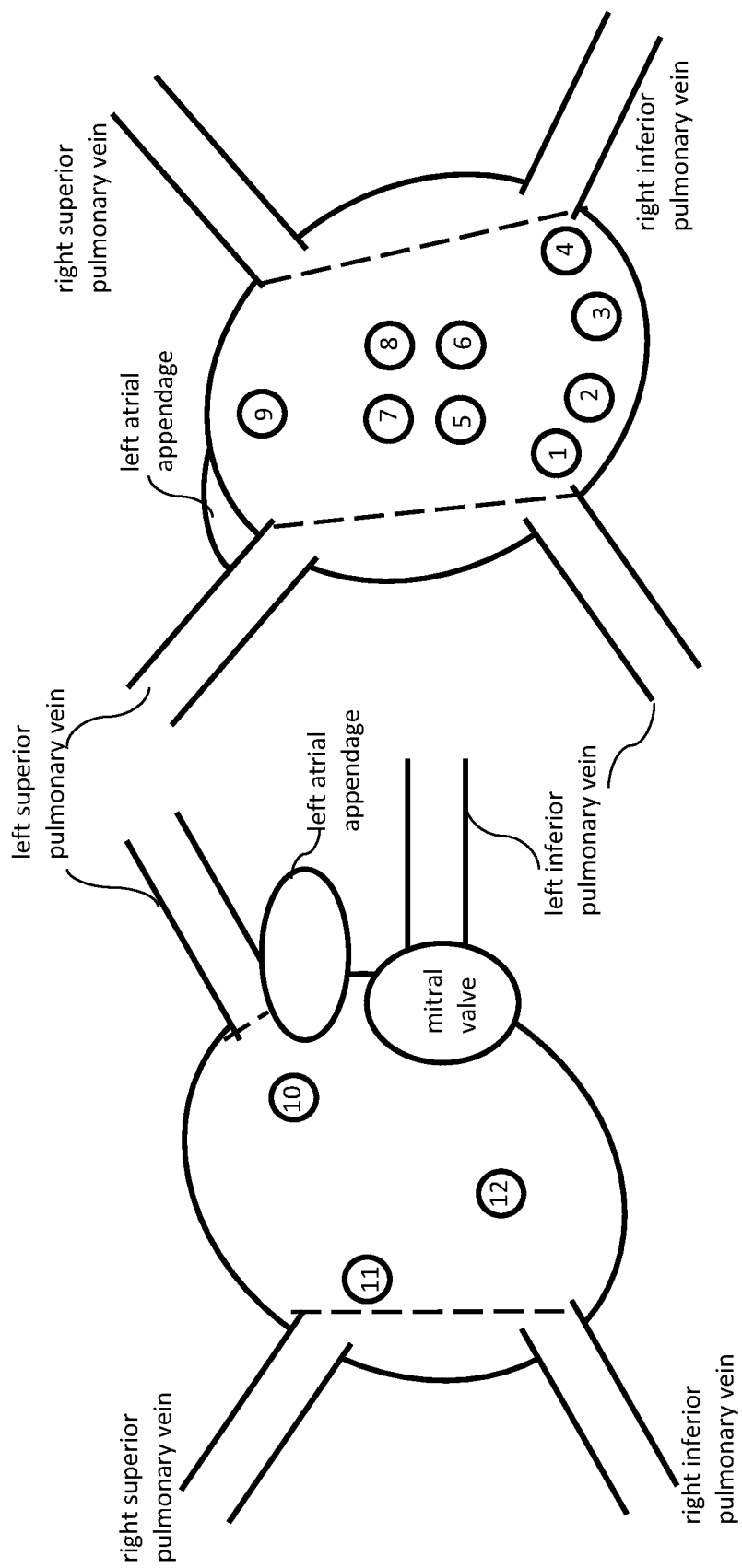
FIG. 19A and FIG. 19B schematically illustrate an atrium mapping positioning method as disclosed herein including an anterior view (FIG. 19A) and a posterior view (FIG. 19B).
Figure 20:
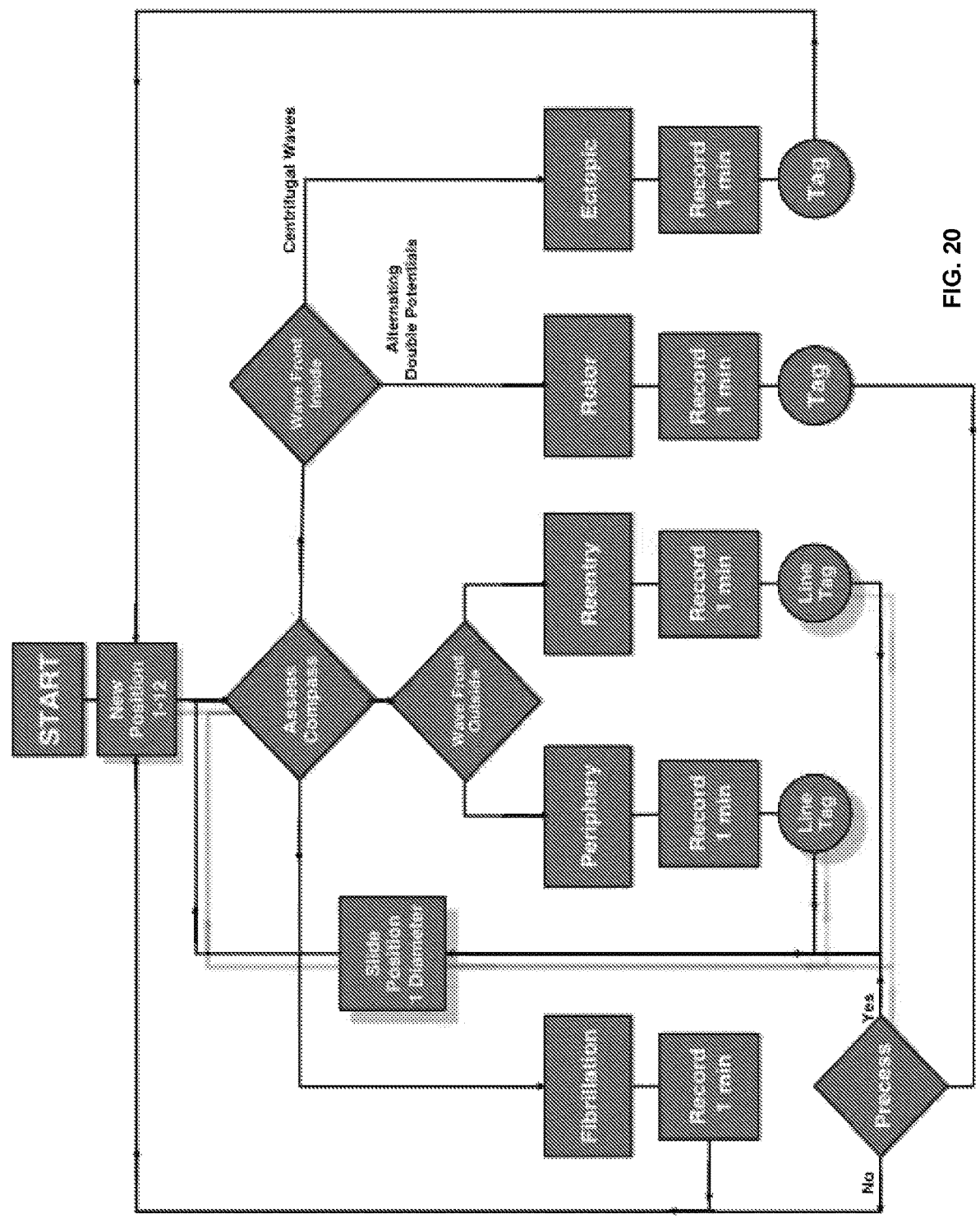
FIG. 20 presents a flow diagram for an atrium mapping positioning method as disclosed herein.

FIG. 19A and FIG. 19B schematically illustrate one mapping process for collecting data across a left atrium. FIG. 20 presents a flow chart of an algorithm approach to collect the data. By way of example, after obtaining merged 3-dimensional left atrial structure according to standard methodology, the catheter including bipolar electrode pairs can be utilized to map the atrium. In general, the catheter can be in communication with a processor and related devices that can include software as is known for processing the electrical signals and providing the information concerning the electrical mapping of the cardiac tissue as output. For instance, a processor in communication with the catheter, e.g., a GE Cardiolab EP Recording Station, can be loaded with suitable recognition and vector analysis software and can receive and analyze the data from the catheter. The processor can also include standard output software as is generally known in the art to provide the resulting data in a preferred fashion, e.g., an electrocardiogram.

According to one mapping scheme, a catheter can be initially placed at Position 1 (FIG. 19B) within a heart chamber (e.g., the left atrium as illustrated) and electrical signals recorded and saved for a period of time, e.g., about 1 minute. If fibrillation only is identified, then the catheter can be moved to Position 2, and recording completed for another period of time. The catheter can be moved sequentially through the positions as indicated on FIG. 19A and FIG. 19B with the information gained at each site stored to form a map of the entire heart chamber. Alternatively, the mapping can be carried out until a trigger or driver is located, upon which the identified site can be ablated, either with or without further mapping of the chamber.

At any position, if a wave front is recorded that by the signal can be recognized as coming from an area outside of the perimeter defined by the electrodes, the earliest and largest amplitude impulses of the electrode pair recordings can provide information with regard to directional deflection of the catheter so as to move the catheter (or redefine the selected electrodes of a larger array) in the direction of incoming propagated waves and thus closer to the fibrillation trigger or driver site. The site can then be tagged as a peripheral site and the tag can include a label of the wave front direction.

According to one embodiment, following tagging of a peripheral site, the perimeter defined by the electrodes can be relocated, e.g., by no more than 1 full diameter of a circular pattern of the bipolar electrodes in the direction toward the source of the wave front and another period of recording can be obtained. The refinement can continue until a rotor core source is found, tagged and recorded for the desired period. Precess direction can be noted and recorded as well.

During a mapping process, an atypical reentrant circuit may be recorded. In this embodiment, the source of a wave front can be a complete discreet circle within the chamber. In this case the catheter peripheral site tags can result in a circle of tag points. The circuit can be labeled as a circuit site and the next position can be examined.

Ectopic foci can also be identified by use of the disclosed catheters. For example, when refining the catheter position by moving into the direction of an incoming peripheral site wave front, an ectopic focus might be found. In this case, rather than an immediate change to alternating sloped double potentials as is the case for a rotor core identification as described above, a centrifugal activation can be seen in which each pole of all of the electrode pairs can present with similar sloping potentials. This site can also be recorded for a period of time; tagged as an ectopic site and the next site can be examined. After all sites in the left atrium have been examined (e.g., all 12 sites in the illustrated example), atrial fibrillation ablation can be carried out.

As shown in FIG. 20, based upon the assessed catheter recording, one of four recording results can be expected (fibrillation, periphery site, rotor core, ectopic focus). Since rotors can precess during the period of recording, three different recording results may be obtained from a single site. First and most commonly it can be expected to find fibrillatory activity. This activity can be recognized by irregular timing of all impulses across most, if not all, electrode pairs. Second, the catheter can record in regions of the peripheral spiral wave. These areas can vary in diameter. In a peripheral site region, fairly regular timing and somewhat stable directional information can be immediately available from the processor. However, since rotors can precess, gradual shifts in cycle lengths and wave front directions can be expected and observed. More rarely, an actual rotor core can be recorded. Rotor core recordings by the disclosed mapping catheters can have an immediate recognizable pattern, including a sudden alternating sloped double potential in all electrode pairs and a doubling of cycle frequency. Using the wave front directional information at a periphery site can also allow the user to locate a perimeter defined by a plurality of bipolar electrodes over a rotor core. The rotor core site can then be tagged and the information saved, for instance in a 3-dimensional map further assessment.

While certain representative embodiments and details have been shown for the purpose of illustrating the subject invention, it will be apparent to those skilled in this art that various changes and modifications may be made therein without departing from the scope of the subject invention.

What is claimed is:

1. A method for mapping cardiac tissue comprising:
   placing an array of electrodes in contact with tissue, the array of electrodes comprising at least three bipolar electrode pairs, wherein at least one of the three bipolar electrode pairs is associated with another bipolar electrode pair to form an inverse input pair of bipolar electrodes;
   measuring electrical signals from the bipolar electrode pairs, each bipolar electrode pair including a first electrode and a second electrode at a distance from and in electrical communication with one another, the electrodes of the at least three bipolar electrode pairs together defining a perimeter around an area, the first and second electrodes of each bipolar electrode pair being located on the perimeter such that the first and second electrodes of each bipolar electrode pair are opposed to one another across the area; and
   analyzing the electrical signals from the bipolar electrode pairs to determine the presence, direction or source of a wave front of depolarization passing through the cardiac tissue.

2. The method of claim 1, wherein the array of electrodes is placed in contact with the cardiac tissue.

3. The method of claim 2, wherein the cardiac tissue is tissue of a subject, the method further comprising placing a second set of electrodes in contact with the skin of the subject and measuring electrical signals from one or more electrodes of the second set.

4. The method of claim 1, further comprising moving the array of electrodes to a one or more successive sites and analyzing the electrical signals from the bipolar electrodes at each successive site to determine the presence, direction, or source of a wave front of depolarization passing through the cardiac tissue.

5. The method of claim 1, wherein the at least three bipolar electrodes are only a portion of the electrodes of the array of electrodes, the method further comprising obtaining and analyzing electrical signals from a different set of bipolar electrode pairs of the array.

6. The method of claim 1, wherein the analysis of the electric signals identifies a reentrant circuit or an ectopic focus in the cardiac tissue and/or identifies the presence or direction of a rotor core within the cardiac tissue.

7. The method of claim 1, the electrical signal analysis demonstrating alternating slopes of double potentials in all of the bipolar electrode pairs, the analysis thus determining that a rotor core is in the cardiac tissue and surrounded by the perimeter defined by the electrodes.

8. The method of claim 1, further comprising separately analyzing the electrical signals from each of the electrodes of the at least three bipolar electrode pairs, the electrical signals being analyzed from each of the electrodes such that adjacent electrodes around the perimeter are analyzed sequentially.

9. A method for mapping cardiac tissue comprising:
placing an array of electrodes in contact with tissue, the array of electrodes comprising at least two bipolar electrode pairs;
obtaining electrical signals from the bipolar electrode pairs, each bipolar electrode pair including a first electrode and a second electrode at a distance from and in electrical communication with one another, the electrodes of the at least two bipolar electrode pairs together defining a perimeter around an area, the first and second electrodes of each bipolar electrode pair being located on the perimeter such that the first and second electrodes of each bipolar electrode pair are opposed to one another across the area; and
analyzing the electrical signals from the bipolar electrode pairs, the electrical signal analysis demonstrating alternating slopes of double potentials in all of the bipolar electrode pairs, the analysis thus determining that a rotor core is in the cardiac tissue and surrounded by the perimeter defined by the electrodes.

10. The method of claim 9, further comprising moving the array of electrodes to one or more successive sites and analyzing the electrical signals from the bipolar electrodes at each successive site.

11. The method of claim 9, wherein the at least two bipolar electrodes are only a portion of the electrodes of the array of electrodes, the method further comprising obtaining and analyzing electrical signals from a different set of bipolar electrode pairs of the array.

12. The method of claim 9, wherein at least one bipolar electrode pair is associated with another bipolar electrode pair to form an inverse input pair of bipolar electrodes.

13. A cardiac mapping catheter, the catheter including an electrode array, the electrode array including at least 3 bipolar electrode pairs, each bipolar electrode pair including a first electrode and a second electrode at a distance from and in electrical communication with one another, the electrodes of the at least three bipolar electrode pairs together defining a perimeter around an area, the first and second electrodes of each bipolar electrode pair being located on the perimeter such that the first and second electrodes of each bipolar electrode pair are opposed to one another across the area, the catheter further including additional electrodes that include additional bipolar electrode pairs, wherein the additional bipolar electrode pairs include a bipolar electrode pair that is associated with one of the at least 3 bipolar electrode pairs in an inverse input pair relationship.

14. The cardiac mapping catheter of claim 13, wherein the distance is about 1.5 centimeters or greater.

15. The cardiac mapping catheter of claim 13, wherein the electrode array is in the form of a grid.

16. The cardiac mapping catheter of claim 13, wherein the catheter is a circular mapping catheter or a basket-type mapping catheter.

* * * * *